United States Patent
Uchiyama et al.

(10) Patent No.: US 9,211,084 B2
(45) Date of Patent: Dec. 15, 2015

(54) MEDICAL GUIDANCE SYSTEM AND CONTROL METHOD OF MEDICAL DEVICE

(75) Inventors: Akio Uchiyama, Tokyo (JP); Atsushi Chiba, Tokyo (JP); Hironao Kawano, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 61 days.

(21) Appl. No.: 12/440,547

(22) PCT Filed: Sep. 14, 2007

(86) PCT No.: PCT/JP2007/067911
§ 371 (c)(1),
(2), (4) Date: Mar. 9, 2009

(87) PCT Pub. No.: WO2008/032815
PCT Pub. Date: Mar. 20, 2008

(65) Prior Publication Data
US 2010/0056866 A1    Mar. 4, 2010

(30) Foreign Application Priority Data

Sep. 14, 2006  (JP) .................................. 2006-249185

(51) Int. Cl.
*A61B 5/05* (2006.01)
*A61B 5/07* (2006.01)
*A61B 1/00* (2006.01)
(Continued)

(52) U.S. Cl.
CPC ............... *A61B 5/07* (2013.01); *A61B 1/00158* (2013.01); *A61B 1/041* (2013.01); *A61B 5/062* (2013.01); *A61B 5/4839* (2013.01); *A61B 5/7232* (2013.01); *A61B 2019/2253* (2013.01)

(58) Field of Classification Search
None
See application file for complete search history.

(56) References Cited

U.S. PATENT DOCUMENTS 5,265,610 A * 11/1993 Darrow et al. ................. 600/410
5,318,025 A *  6/1994 Dumoulin et al. ............ 600/417
(Continued)

FOREIGN PATENT DOCUMENTS

JP    2005-058430    3/2005
JP    2005-245963    9/2005
(Continued)

OTHER PUBLICATIONS

Extended Supplementary European Search Report dated Jul. 9, 2015 from related European Application No. 07 80 7318.6.

*Primary Examiner* — Nicholas Evoy
(74) *Attorney, Agent, or Firm* — Scully, Scott, Murphy & Presser, PC

(57) ABSTRACT

A medical guidance system and a control method of a medical device are provided, which may increase the drive force of a medical device and improve controllability thereof. The medical guidance system has a medical device that includes a biologic information acquisition unit that acquires biologic information of the inside of a body cavity and a magnet that generates drive force in response to a magnetic field exerted from the outside of a body, a magnetic field generation unit 101 that generates the magnetic field to be exerted on the magnet from the outside of a body, and a displacement detection unit 105 that detects displacement being an angle formed between the magnetization direction of the magnet and the field direction of the magnetic field generated by the magnetic field generation unit 101 at the position of the medical device; wherein the magnetic field generation unit 101 is controlled based on the displacement.

14 Claims, 21 Drawing Sheets

(51) Int. Cl.
*A61B 1/04* (2006.01)
*A61B 5/06* (2006.01)
*A61B 5/00* (2006.01)
*A61B 19/00* (2006.01)

(56) References Cited

U.S. PATENT DOCUMENTS

| | | | | |
|---|---|---|---|---|
| 5,377,678 | A * | 1/1995 | Dumoulin et al. | 600/424 |
| 6,511,417 | B1 * | 1/2003 | Taniguchi et al. | 600/117 |
| 6,711,429 | B1 * | 3/2004 | Gilboa et al. | 600/407 |
| 6,757,557 | B1 * | 6/2004 | Bladen et al. | 600/424 |
| 6,949,068 | B2 * | 9/2005 | Taniguchi et al. | 600/117 |
| 7,173,507 | B2 * | 2/2007 | Ries | 335/299 |
| 7,174,202 | B2 * | 2/2007 | Bladen et al. | 600/424 |
| 7,509,158 | B2 * | 3/2009 | Minai et al. | 600/424 |
| 7,536,217 | B2 * | 5/2009 | Minai et al. | 600/424 |
| 7,623,904 | B2 * | 11/2009 | Uchiyama et al. | 600/424 |
| 7,697,970 | B2 * | 4/2010 | Uchiyama et al. | 600/407 |
| 7,711,408 | B2 * | 5/2010 | Uchiyama et al. | 600/424 |
| 7,841,981 | B2 * | 11/2010 | Kawano et al. | 600/118 |
| 7,935,047 | B2 * | 5/2011 | Yoshida et al. | 600/117 |
| 8,545,397 | B2 * | 10/2013 | Tanaka | 600/117 |
| 2003/0187347 | A1 * | 10/2003 | Nevo et al. | 600/424 |
| 2003/0229268 | A1 * | 12/2003 | Uchiyama et al. | 600/109 |
| 2005/0052178 | A1 * | 3/2005 | Ries | 324/207.23 |
| 2005/0085696 | A1 * | 4/2005 | Uchiyama et al. | 600/160 |
| 2005/0093544 | A1 * | 5/2005 | Ries | 324/318 |
| 2005/0183733 | A1 * | 8/2005 | Kawano et al. | 128/899 |
| 2005/0216231 | A1 | 9/2005 | Aoki et al. | |
| 2006/0063974 | A1 * | 3/2006 | Uchiyama et al. | 600/114 |
| 2007/0191671 | A1 * | 8/2007 | Kawano et al. | 600/12 |
| 2007/0191758 | A1 * | 8/2007 | Hunter et al. | 604/22 |
| 2007/0219410 | A1 * | 9/2007 | Onoda et al. | 600/117 |
| 2007/0221233 | A1 * | 9/2007 | Kawano et al. | 128/899 |
| 2007/0232854 | A1 * | 10/2007 | Miyake et al. | 600/117 |
| 2007/0236213 | A1 * | 10/2007 | Paden et al. | 324/228 |
| 2007/0238922 | A1 * | 10/2007 | Oda et al. | 600/117 |
| 2007/0238987 | A1 * | 10/2007 | Minai et al. | 600/424 |
| 2007/0238988 | A1 * | 10/2007 | Minai | 600/424 |
| 2007/0244388 | A1 * | 10/2007 | Sato et al. | 600/424 |
| 2007/0255087 | A1 * | 11/2007 | Minai | 600/12 |
| 2007/0260139 | A1 * | 11/2007 | Minai et al. | 600/420 |
| 2007/0265496 | A1 * | 11/2007 | Kawano et al. | 600/109 |
| 2007/0270628 | A1 * | 11/2007 | Kawano et al. | 600/12 |
| 2008/0009675 | A1 * | 1/2008 | Kura | 600/137 |
| 2008/0009714 | A1 * | 1/2008 | Oda | 600/424 |
| 2008/0039688 | A1 * | 2/2008 | Minal et al. | 600/117 |
| 2008/0294006 | A1 * | 11/2008 | Uchiyama et al. | 600/118 |
| 2008/0306340 | A1 * | 12/2008 | Uchiyama et al. | 600/117 |

FOREIGN PATENT DOCUMENTS

| | | |
|---|---|---|
| JP | 2006-075537 | 3/2006 |
| JP | 2006-149688 | 6/2006 |
| WO | WO 2006064972 A1 * | 6/2006 |

* cited by examiner

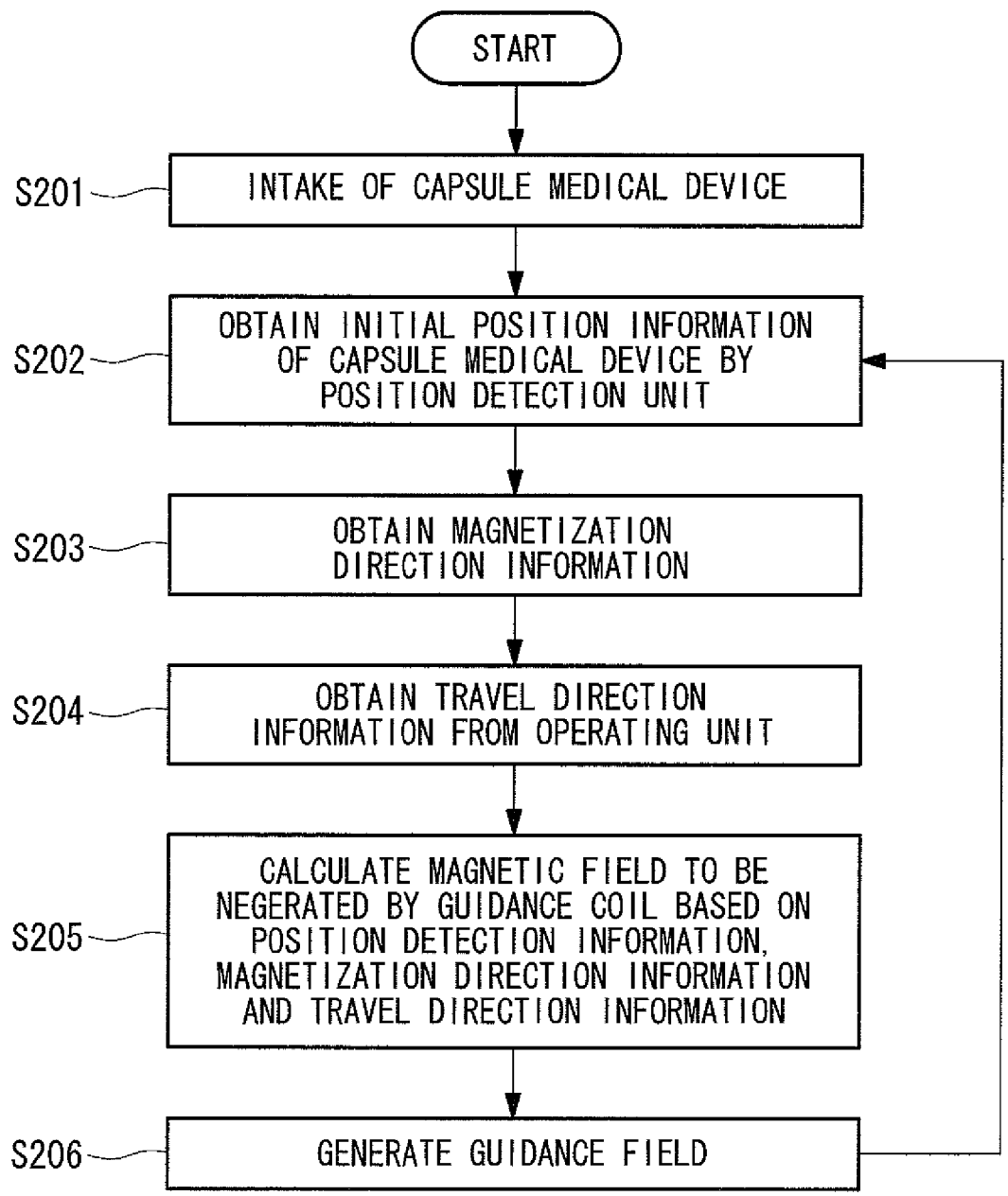

MEDICAL GUIDANCE SYSTEM AND CONTROL METHOD OF MEDICAL DEVICE

TECHNICAL FIELD

The present invention relates to a medical guidance system that guides a medical device inserted into a body cavity, and a control method of the medical device.

BACKGROUND ART

As a method of guiding a medical device such as a capsule endoscope within a body cavity, a magnetic guidance technique of a medical device has been developed, in which a magnet is incorporated in the medical device, and a magnetic field is applied to the magnet from the outside, so that the position and the direction of the medical device are controlled (for example, refer to patent citations 1 to 3.

Patent Citation 1: Japanese Unexamined Patent Application, Publication No. 2006-075537
Patent Citation 2: Japanese Unexamined Patent Application, Publication No. 2005-058430
Patent Citation 3: Japanese Unexamined Patent Application, Publication No. 2006-149688

DISCLOSURE OF INVENTION

When the guidance control is performed, the magnetization direction of a magnet is desirably aligned with the direction of a magnetic field applied at a disposed position of a medical device.

However, the magnetization direction of the magnet may not correspond to the direction of an applied magnetic field, for example, in the case that a magnet is allowed to generate torque in order to change the direction of a medical device, or in the case that motion of a capsule is restricted due to friction between a medical device and a coeliac tissue, leading to a problem in which the medical device cannot be guided in the intended direction.

In previous position detection units, the phase around the longitudinal axis of a medical device has not been able to be measured. Therefore, the phase around the longitudinal axis has been estimated based on the detected position of the medical device and an induction field formed around the medical device.

However, since the phase around the longitudinal axis of the medical device is not always oriented in the same direction as the direction of the induction field, a phase difference may occur between an actual phase and an estimated phase. A phase difference will cause a problem of reduction in magnetic attraction for driving the medical device, reduction in magnetic torque for rotationally driving the medical device, or unstable guidance of the medical device.

The invention has been made to solve this problem, and an object of the invention is to provide a medical guidance system which may increase the drive force of a medical device and improve controllability thereof.

To achieve this object, the invention provides the following means.

A first aspect of the invention provides a medical guidance system having a medical device including a biologic information acquisition unit that acquires biologic information of the inside of a body cavity, and a magnet that generates drive force in response to a magnetic field exerted from the outside of a body; a magnetic field generation unit that generates the magnetic field to be exerted on the magnet from the outside of a body; and a displacement detection unit that detects displacement being an angle formed between the magnetization direction of the magnet and the field direction of the magnetic field generated by the magnetic field generation unit at the position of the medical device; wherein the magnetic field generation unit is controlled based on the displacement.

A second aspect of the invention provides a control method of a medical device including a biologic information acquisition unit that acquires biologic information of the inside of a body cavity, and a magnet that generates drive force in response to a magnetic field exerted from the outside of a body, wherein displacement being an angle formed between the magnetization direction of the magnet and the field direction of the magnetic field exerted on the magnet from the outside of a body is detected, and the magnetic field exerted on the magnet from the outside of a body is controlled based on the displacement.

According to the first and second aspects of the invention, the field direction of the magnetic field exerted on the magnet is controlled based on the displacement being the angle formed between the magnetization direction of the magnet and the field direction of the magnetic field applied to the magnet from the outside of a body. The displacement causes attraction, torque, or the like to be exerted on the magnet, and the medical device is guided thereby.

In this way, the field direction of the magnetic field exerted on the magnet is controlled based on the displacement. This may prevent the phenomenon in which the medical device is unstably guided due to misalignment between the magnetization direction and the field direction. That is, the displacement is controlled within a predetermined range. This may prevent reduction in magnetic attraction for driving the medical device and reduction in magnetic torque for rotationally driving the medical device. Consequently, the medical device can be stably guided.

The attraction or torque exerted on the medical device is determined by the displacement, the intensity of the magnetic field exerted on the magnet, and the like. Therefore, the magnetic field exerted on the magnet is controlled so that the attraction or torque exerted on the medical device can be controlled and so that, consequently, the medical device can be stably guided.

In the first aspect of the invention, desirably, the medical guidance system further has a position detection unit that detects at least one of a position and direction of the medical device, and the magnetic field generation unit is controlled based on the displacement and on at least one of the position and direction of the medical device.

In the second aspect of the invention, desirably, at least one of a position and direction of the medical device is detected, and the magnetic field exerted on the magnet from the outside of a body is controlled based on the displacement and on at least one of the position and direction of the medical device.

According to this, the field direction of the magnetic field exerted on the magnet is controlled based on not only the displacement, but also at least one of the position and direction of the medical device. Since the magnet is provided in the medical device, the position and the direction of the medical device can be easily converted into the position and the direction of the magnet. Moreover, the field direction of the magnetic field exerted on the magnet may be changed based on the positional relationship between the magnet and the place at which the magnetic field is generated, namely, the magnetic field generation unit. Therefore, the field direction of the magnetic field exerted on the magnet is controlled based on at least one of the position and direction of the medical device. Thereby, the field direction of the magnetic field exerted on the magnet is appropriately controlled compared with a case in which control is not performed based on at least one of the position and direction of the medical device. Consequently, the medical device can be stably guided.

As the position of the medical device, for example, coordinate values on the X axis, the Y axis, and the Z axis of a Cartesian coordinate system can be exemplified, and as the direction, phases around the X axis, Y axis, and Z axis can be exemplified.

In the first aspect of the invention, desirably, the displacement detection unit includes a field detection unit that detects the field intensity of a magnetic field formed at the position of the medical device by the magnetic field generation unit, and a displacement calculation unit that calculates the displacement based on the detected field intensity and on the field intensity of the magnetic field formed at the position of the medical device.

In the second aspect of the invention, desirably, when the displacement is detected, the field intensity of the magnetic field formed at the position of the medical device is detected, and the displacement is calculated based on the detected field intensity and on the field intensity of the magnetic field formed at the position of the medical device.

According to this, when a magnetic field is injected at a predetermined angle with respect to a sensitivity axis for detecting the field intensity, a field intensity is detected, and the value of the field intensity is given by multiplying the intensity of the injected field by the cosine of the angle. Therefore, when the detected field intensity and the field intensity of the magnetic field formed at the position of the medical device are known, the angle formed between the direction of the magnetic field and the sensitivity axis may be calculated. Since the direction of the sensitivity axis and the magnetization direction of the magnet are in a predetermined, positional relationship, displacement being an angleformed between the magnetization direction of the magnet and the field direction of the magnetic field applied to the magnet from the outside of a body can be calculated.

In the first aspect of the invention, desirably, the displacement detection unit includes an external field detection unit that detects the magnetic field formed by the magnet on the outside of the medical device and a displacement calculation unit that calculates the magnetization direction of the magnet from field information detected by the external field detection unit and calculates the displacement based on the calculated magnetization direction.

In the second aspect of the invention, desirably, when displacement is detected, a magnetic field formed by the magnet is detected on the outside of the medical device, the magnetization direction of the magnet is calculated from the detected magnetic field, and the displacement is calculated based on the calculated magnetization direction.

According to this, a magnetic field formed in the periphery of the medical device by the magnet is detected, and the magnetization direction of the magnet is calculated based on the detected field information. Since the calculated magnetization direction approximately corresponds to the magnetization direction of the magnet, the displacement can be calculated based on the calculated magnetization direction.

In the first aspect of the invention, desirably, the displacement detection unit includes an alternating field generation unit that forms an alternating field in the working area of the medical device from the outside, an alternating field detection unit that detects the field intensity of the alternating field in the medical device, and a displacement calculation unit that calculates the displacement based on the detected field intensity of the alternating field and on the field intensity of the alternating field in the medical device.

In the second aspect of the invention, desirably, when displacement is detected, an alternating field is formed in the working area of the medical device from the outside, the field intensity of the alternating field is detected in the medical device, and the displacement is calculated based on the detected field intensity of the alternating field and on the field intensity of the alternating field in the medical device.

According to this, when the alternating field is injected at a predetermined angle with respect to a sensitivity axis for detecting the field intensity, a field intensity having a value given by multiplying the intensity of the injected field by a cosine of the angle, is detected. Therefore, when the detected field intensity, and the field intensity of the alternating field formed at the position of the medical device are known, an angle formed between the direction of the magnetic field and the sensitivity axis may be calculated. Since the direction of the sensitivity axis and the magnetization direction of the magnet are in a predetermined, positional relationship, displacement being an angle can be calculated, the angle being formed by the magnetization direction of the magnet and the field direction of the magnetic field applied to the magnet from the outside of a body.

In the first aspect of the invention, desirably, the displacement detection unit includes an alternating field generation unit that forms an alternating field in the working area of the medical device from the outside, an alternating field detection unit that detects the alternating field in the medical device, and a displacement calculation unit that calculates the direction of the magnet based on the alternating field information detected by the alternating field detection unit and calculates the displacement based on the calculated direction of the magnet.

In the second aspect of the invention, desirably, when the displacement is detected, an alternating field is formed in the working area of the medical device from the outside, the alternating field is detected in the medical device, the direction of the magnet is calculated based on the detected alternating field information, and the displacement is calculated based on the calculated direction of the magnet.

According to this, the magnetization direction of the magnet is calculated based on the detected alternating field information. Since the calculated magnetization direction approximately corresponds to the magnetization direction of the magnet, the displacement can be calculated based on the calculated magnetization direction.

In the first aspect of the invention, the intensity of a magnetic field generated by the magnetic field generation unit is desirably changed based on the displacement.

In the second aspect of the invention, the intensity of a magnetic field exerted on the magnet from the outside of a body is desirably changed based on the displacement.

According to this, the intensity of the magnetic field exerted on the magnet from the outside of a body is changed based on the displacement. Thereby, attraction or torque exerted on the medical device can be controlled, and, consequently, the medical device is stably guided.

According to the medical guidance system and the control method of a medical device of the invention, the direction of a magnetic field exerted on a magnet is controlled based on displacement being an angle formed between the magnetization direction of the magnet and the direction of a magnetic field applied to the magnet from the outside of a body. Thereby, attraction or torque exerted on a medical device may be controlled, leading to the advantages of increased drive force of the medical device and improvement in controllability thereof.

BRIEF DESCRIPTION OF DRAWINGS

FIG. 21 is a flowchart for illustrating the calculation method of the angle formed between the magnetization direction and the field direction in an embodiment of the second embodiment of the invention.

EXPLANATION OF REFERENCES

1, 201, 301, 401, 501, 601: capsule medical device system (medical guidance system)

3, 203, 403, 503, 603: capsule medical device (medical device)
9: imaging unit (biologic information acquisition unit)
13: magnetic sensor (field detection unit)
27: permanent magnet (magnet)
79: position detection field generation unit (alternating field generation unit)
91: position/direction calculation unit (position detection unit)
93: magnetic-field/magnetization-direction angular-difference calculation unit (displacement detection unit)
101: guidance coils (field generation unit)
105: field/magnetization displacement determination unit (displacement detection unit)
213: magnetization direction detection coil (alternating field detection unit)
413: magnetization direction detection coil (field detection unit)
568: field sensors (external field detection unit)

BEST MODE FOR CARRYING OUT THE INVENTION

First Embodiment

Hereinafter, a first embodiment of the invention is described with reference to FIGS. 1 to 8.

Figure 1:
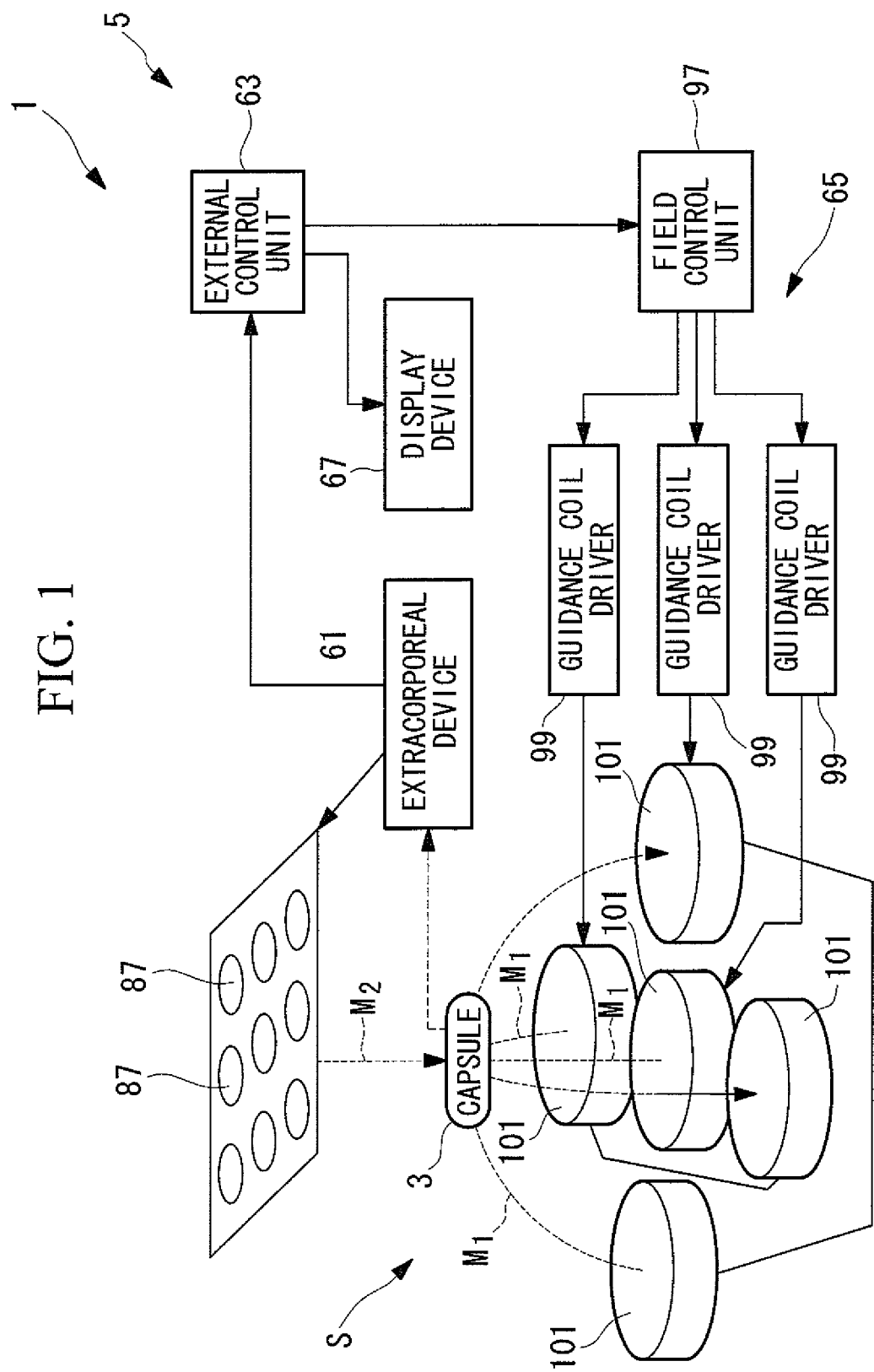
FIG. 1 is a general block diagram showing a capsule medical device system according to a first embodiment of the invention.
Figure 2:
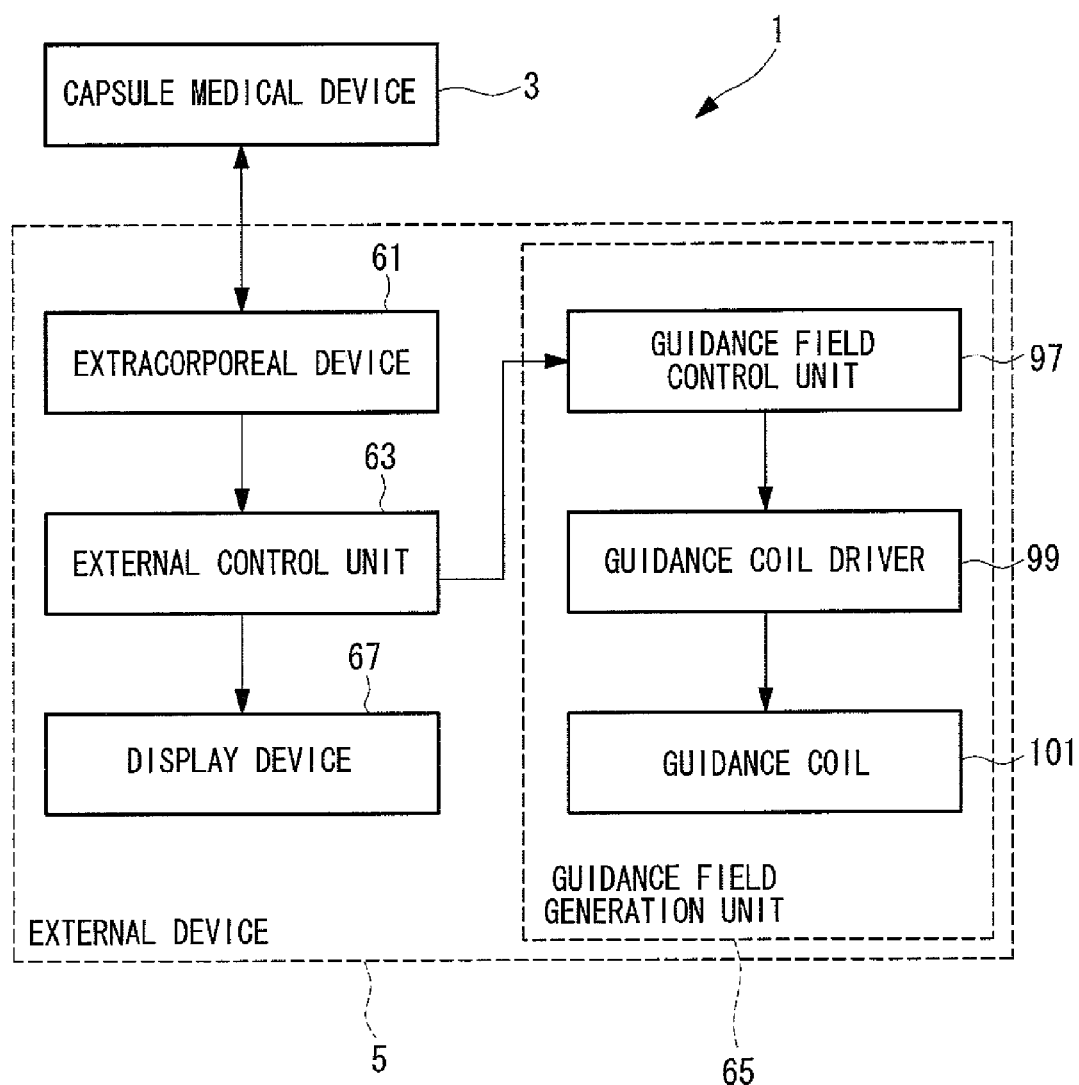
FIG. 2 is a block diagram showing the capsule medical device system of FIG. 1.

FIG. 1 shows a general block diagram of a capsule medical device system according to the embodiment, and FIG. 2 shows a block diagram of the capsule medical device system of FIG. 1.

The capsule medical device system (medical guidance system) 1 according to the embodiment has a capsule medical device 3 to be put into the body cavity of a subject (not shown) and an external device 5 disposed outside the body of the subject as shown in FIGS. 1 and 2.

Figure 3:
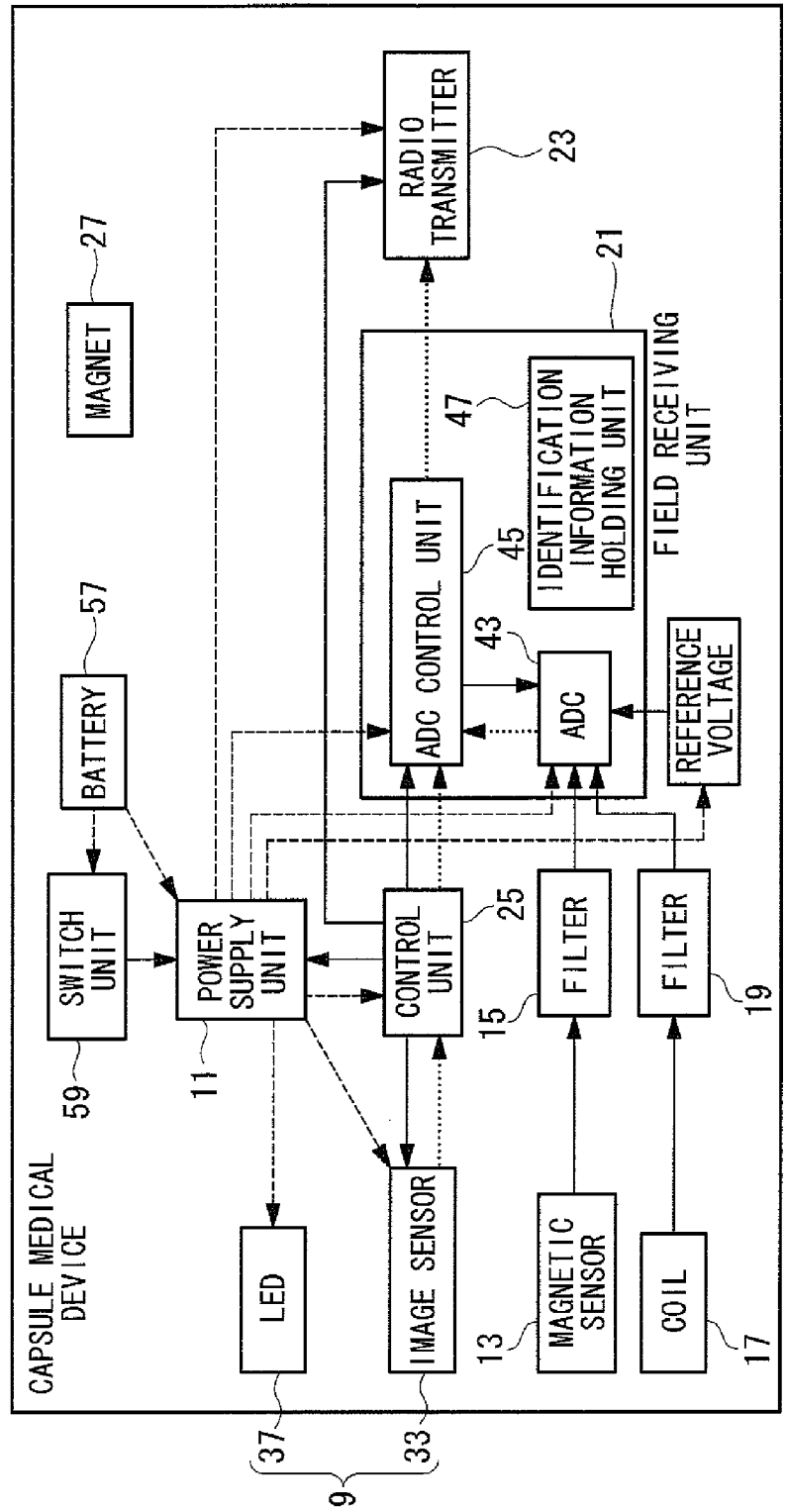
FIG. 3 is a block diagram showing a capsule medical device in FIG. 1.
Figure 4:
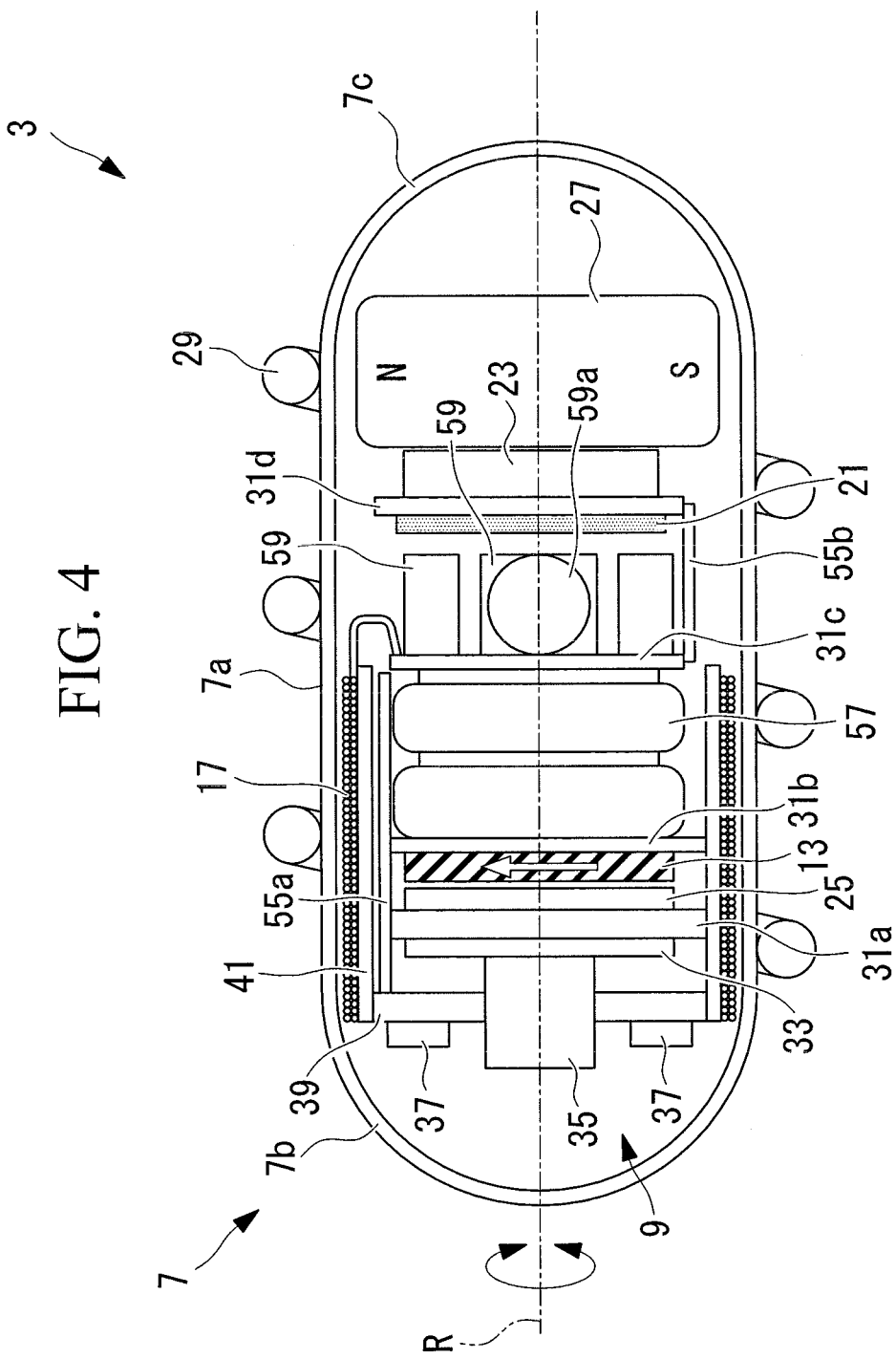
FIG. 4 is a longitudinal section view showing the capsule medical device of FIG. 3.

FIG. 3 shows a block diagram of the capsule medical device according to the embodiment, and FIG. 4 shows a longitudinal section view of the capsule medical device of FIG. 3.

As shown in FIGS. 3 and 4, the capsule medical device (medical device) 3 includes a package 7 that stores various devices within the package, an imaging unit (biologic information acquisition unit) 9 that acquires an image (biologic information) of the inside of a body cavity, a power supply unit 11 that supplies power to the various devices within the package 7, a magnetic sensor (field detection unit) 13 that generates a detection signal in response to a magnetic field M2, a sensor filter 15 that filters the detection signal, a field sensor coil (hereinafter, simply referred to the coil) 17 which generates an induction signal in response to a magnetic field M1 or M2, a coil filter 19 that filters the induction signal, a field receiving unit 21 that processes the induction signal and detection signal, a radio transmitter 23 that transmits the processed induction signal and the detection signal to the outside of a body, a control unit 25 that controls the power supply 11, the imaging unit 9, an induction signal processing unit 9, and the radio transmitter 23, and a permanent magnet (magnet) 27 that generates drive force in response to the magnetic field M1 or M2.

The package 7 is formed by a cylindrical capsule body 7a, which transmits infrared rays, with a longitudinal axis R of the capsule medical device 3 as a central axis, a transparent, semispherical head portion 7b covering the front of the capsule body 7a, and a semispherical tail portion 7c covering the back of the capsule body 7a, which collectively form a capsule container having a sealed, watertight structure.

A spiral portion 29, which is formed by spirally winding a wire having a circular section around the longitudinal axis R, is provided on an outer circumferential face of the capsule body 7a of the package 7.

The imaging unit 9 takes a picture of the inside of a body cavity of a subject to acquire an image (biologic information). The imaging unit 9 has an image sensor 33 disposed on a surface at the head portion 7b side of a substrate 31a disposed approximately vertically to the longitudinal axis R, a lens group 35 that forms an image of the inside of the body cavity of the subject on the image sensor 33, and LEDs (Light Emitting Diodes) 37 that illuminate the inside of the body cavity.

The image sensor 33 converts the light of the image formed via the head portion 7b and the lens group 35 into an electric signal (image signal), and outputs the signal to the control unit 25. For the image sensor 33, an imaging device such as CMOS (Complementary Metal Oxide Semiconductor) or CCD (Charge Coupled Device) may be used.

A plurality of LED 37 are disposed on a support member 39 disposed near the head portion 7b with respect to the substrate 31a with intervals in a circumferential direction about the longitudinal axis R.

The magnetic sensor 13 generates a detection signal in response to the magnetic field M2 applied from an external device 5, and disposed within a coil 17 such that the sensitivity axis is oriented along the direction perpendicular to the longitudinal axis R (for example, vertical direction in the relevant figure). Therefore, the magnetic sensor 13 is disposed such that the sensitivity axis thereof is along the magnetization direction of the permanent magnet 27. The detection signal from the magnetic sensor is inputted into the sensor filter 15.

As the magnetic sensor 13, a known magnetic sensor may be used, including an MI sensor (magnetic impedance sensor), an MR element (magnetic resistance element), a GMR sensor (giant magnetic resistance sensor), a flux gate sensor, or a Hall element, which is not particularly limited.

As described above, a magnetic sensor 13 having a uniaxial sensitivity axis may be used, or a magnetic sensor 13 having a biaxial or triaxial sensitivity axis may be used, which is not particularly limited. The use of a magnetic sensor 13 with a biaxial or triaxial sensitivity axis, allows for more accurate detection of the displacement direction of a magnetic field, and for higher performance in the subsequent control.

The sensor filter 15 is provided, for example, on the substrate 31a, and includes a primary high-pass filter having, for example, a cutoff frequency of about 1 kHz. The sensor filter 15 receives a detection signal from the magnetic sensor 13, and outputs a filtered detection signal to an A/D converter 43.

The coil 17 generates an induction signal in response to the magnetic field M1 or M2 applied from the external device 5, and is disposed while being cylindrically wound on a radially inner part of the capsule body 7a of the package 7. In the figure, a symbol 41 shows a bobbin that is formed in a cylindrical shape having a central axis that corresponds approximately to the longitudinal axis R. The coil 17 is wound on an outer circumferential face of the bobbin 41.

Thus, the coil 17 is disposed such that the opening direction of the coil is perpendicular to the magnetization direction of the permanent magnet 27. This results in a configuration where the magnetic field formed by the permanent magnet 27 is prevented from passing through the inside of the coil 17, and thus may not affect an induction signal generated by the coil 17.

The induction signal generated by the coil 17 is inputted into the coil filter 19.

The coil filter 19 is provided, for example, on the substrate 31a, and includes a primary high-pass filter having, for example, a cutoff frequency of about 1 kHz. The coil filter 19 receives an induction signal from the coil 17, and outputs a filtered induction signal to the A/D converter 43.

The field receiving unit 21 processes the induction signal, which passes through the coil filter 19, and the detection signal, which passes through the sensor filter 15. The field receiving unit 21 includes the A/D converter (mentioned as ADC in the relevant figure) 43, an A/D converter control unit (mentioned as ADC control unit in the relevant figure) 45, and an identification information holding unit 47.

The A/D converter 43 converts the induction signal, which passes through the coil filter, and the detection signal, which passes through the sensor filter 15, into digital signals.

The A/D converter control unit 45 controls the A/D converter 43 and transfers the induction signal and the detection signal outputted from the A/D converter 43 and the image signal acquired by the image sensor 33 to the radio transmitter 23 at a predetermined timing.

The identification information holding unit 47 stores information including the position of the coil 17, the relative angle of the opening direction of the coil 17, the magnetization direction of the permanent magnet 27, and the relative position between the coil 17 and the permanent magnet 27. When the capsule medical device 3 is operated, the information stored in the identification information holding unit 47 is transmitted to an extracorporeal device 61 via the radio transmitter 23 at least once.

Figure 5:
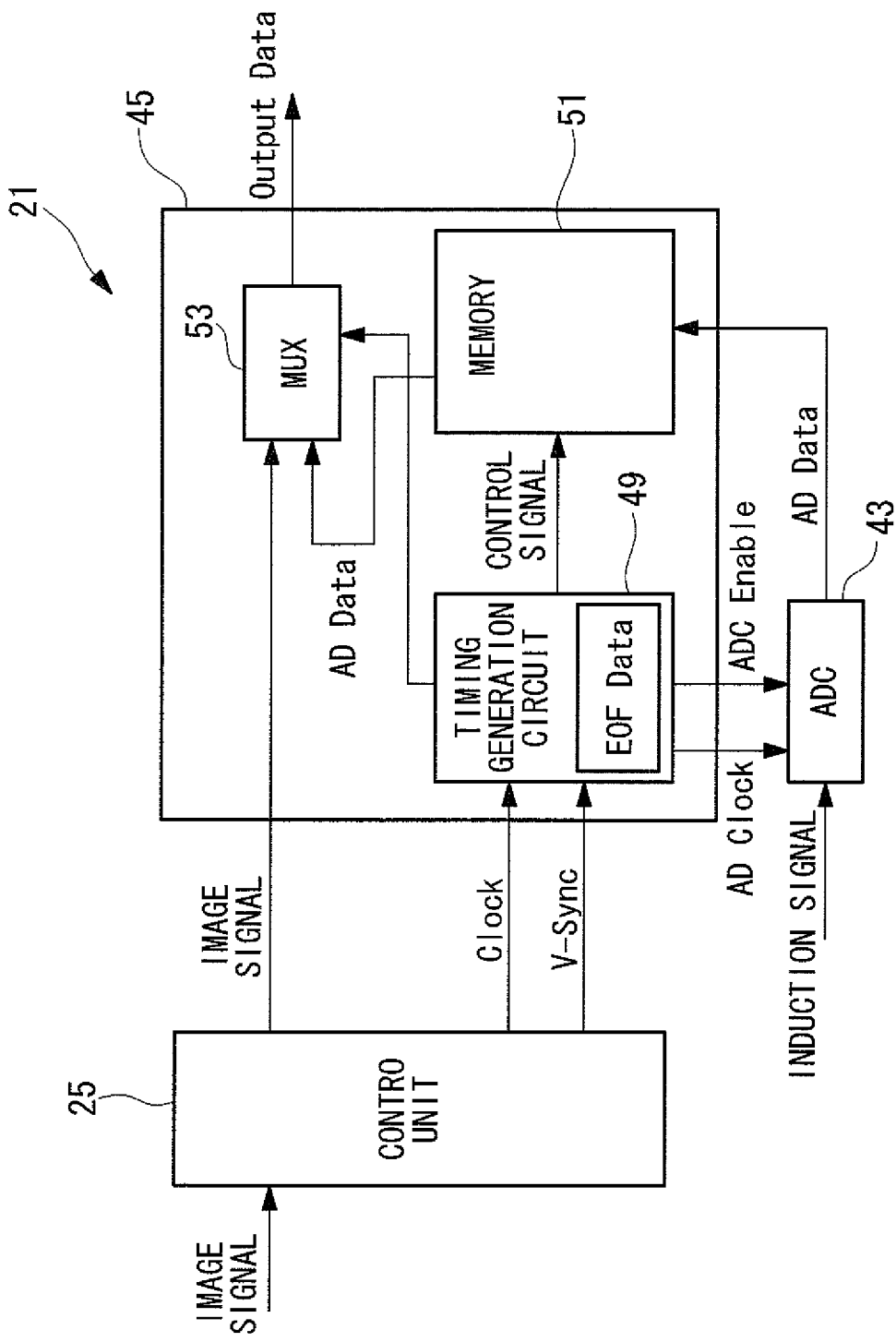
FIG. 5 is a block diagram showing an induction signal processing unit incorporated in the capsule medical device of FIG. 3.

FIG. 5 shows a block diagram of the induction signal processing unit incorporated in the capsule medical device of FIG. 3.

More specifically, as shown in FIG. 5, the A/D converter control unit 45 includes a timing generation circuit 49, a memory 51, and a multiplexer 53 and is connected to the control unit 25.

The timing generation circuit 49 generates a timing signal based on a clock signal Clock received from the control unit 25, and a synchronizing signal (for example, vertical synchronizing signal V-Sync) obtained from an image signal inputted into the control unit 25. The timing generation circuit 49 outputs a clock signal (AD Clock) and an A/D conversion enable signal to the A/D converter 43.

The memory 51 stores a digital induction signal outputted from the A/D converter 43.

The multiplexer 53 is connected to the memory 51, the timing generation circuit 49, and the control unit 25 and switches between an image signal from the control unit 25 and an induction signal from the memory 51 in accordance with a timing signal from the timing generation circuit 49.

The control unit 25 is electrically connected to a battery 57 via substrates 31a to 31d and flexible boards 55a and 55b, electrically connected to the image sensor 33 via the substrate 31a, and electrically connected to the LED 37 via the substrate 31a, the flexible board 55a and the support member 39. The control unit 25 outputs an image signal acquired by the image sensor 33 to the A/D converter control unit 45 and controls the on/off of each of the image sensor 33 and the LED 37.

The control unit 25 controls the radio transmitter 23 so that the radio transmitter transmits a signal to the outside, the signal being outputted from the multiplexer 53 of the A/D converter control unit 45 to the radio transmitter.

That is, the radio transmitter 23 transmits an image signal of a predetermined length and an induction signal to the outside in a consecutive data form.

The permanent magnet 27 generates drive force in response to the magnetic field M1 or M2 applied from the external device 5. The permanent magnet 27 is disposed at the tail portion 7c side of the radio transmitter 23. The permanent magnet 27 is disposed or magnetized such that it has a magnetization direction (magnetic pole) that is perpendicular to the longitudinal axis R (for example, the vertical direction in the relevant figure).

Switch units 59 disposed on the substrate 31c are provided at the head portion 7b side of the permanent magnet 27. Each of the switch units 59 has an infrared sensor 59a and is electrically connected to a power source unit 11 and to the battery 57 via the substrate 31c and the flexible board 55a.

The switch units 59 are disposed with even intervals in a circumferential direction about the longitudinal axis R such that each infrared sensor 59a faces the outside in a diametrical direction. While an example where four switch units 59 are disposed is described in the embodiment, the number of the switch units 59 is not limited to four, and any number is acceptable.

The battery 57 is disposed while being interposed between the substrates 31b and 31c at a head portion 7b side of the switch units 59.

Figure 6:
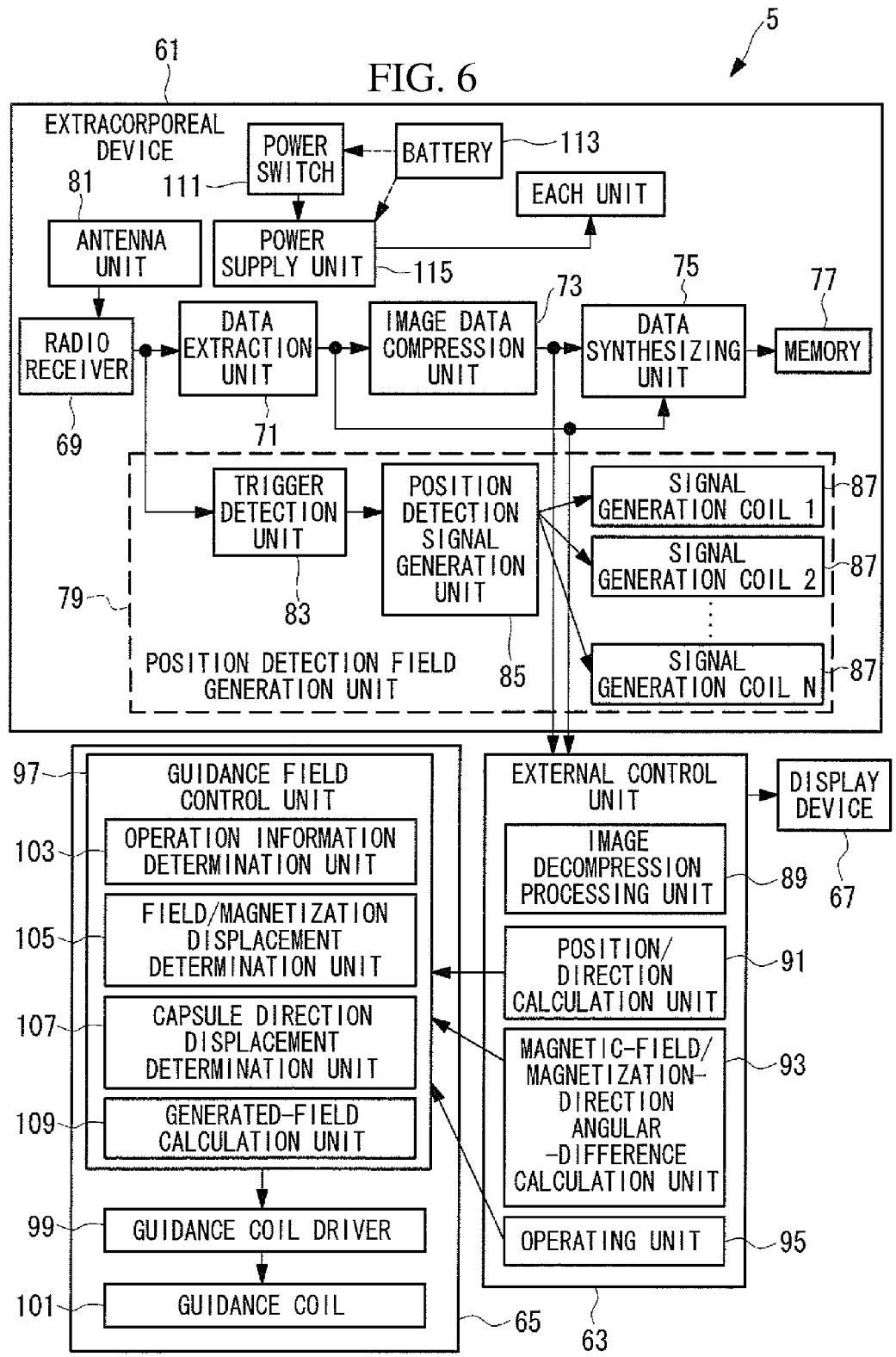
FIG. 6 is a block diagram showing an external device in the capsule medical device system of FIG. 1.

FIG. 6 shows a block diagram of the external device in the capsule medical device system of FIG. 1.

The external device 5 is disposed outside the body of a subject, performs position detection and guidance of the capsule medical device 3, and displays a picture taken by the capsule medical device 3. As shown in FIGS. 2 and 6, the external device 5 includes the extracorporeal device 61 that generates a magnetic field M2 for position detection, an external control unit 63 that calculates the position and the direction of the capsule medical device 3, a guidance field generation unit 65 that generates a magnetic field M1 for guidance, and a display device 67 that displays an image based on an image signal outputted from the external control unit 63.

The extracorporeal device 61 receives a signal sent from the capsule medical device 3, and generates the position detection field M2. The extracorporeal device 61 includes a radio receiver 69, a data extraction unit 71, an image data compression unit 73, a data synthesizing unit 75, a memory 77, and a position detection field generation unit 79.

The radio receiver 69 receives an image signal, an induction signal, and a detection signal sent from the capsule medical device 3 via the antenna unit 81.

The data extraction unit 71 extracts the induction signal and the detection signal from the signals received by the radio receiver 69. The signals received by the radio receiver 69 include the image signal, induction signal, and detection signal. Since the image signal has a predetermined length, the data extraction unit 71 can easily separate the image signal from the induction signal and detection signal that follow the image signal.

The image data compression unit 73 compresses the image signal separated by the data extraction unit 71.

The data synthesizing unit 75 synthesizes the image signal compressed by the image data compression unit 73 and the separated induction signal.

The memory 77 stores data synthesized by the data synthesizing unit 75.

The position detection field generation unit 79 generates the position detection field M2 based on the signal received by the radio receiver 69. The position detection field generation unit 79 includes a trigger detection unit 83, a position detection signal generation unit 85, and a plurality of signal generation coils 87.

The trigger detection unit 83 detects a trigger signal included in image information, for example, a vertical synchronizing signal V-Sync.

The position detection signal generation unit 85 outputs a position detection signal at timing with a trigger signal detected by the trigger detection unit 83 as a reference.

The signal generation coils 87 generate the position detection field M2 based on the signal outputted from the position detection signal generation unit 85.

The external control unit 63 generates an image and calculates the position and the direction of the capsule medical device 3 based on the signal received by the extracorporeal device 61. The external control unit 63 includes an image decompression processing unit 89, a position/direction calculation unit (position detection unit) 91, a magnetic-field/magnetization-direction angular-difference calculation unit (displacement detection unit) 93, and an operating unit 95.

The image decompression processing unit 89 decompresses a compressed image signal sent from the extracorporeal device 61 and outputs the decompressed signal to the display device 67.

The position/direction calculation unit 91 calculates the position and the direction of the capsule medical device 3 based on an induction signal sent from the extracorporeal device 61 and outputs the calculated signal to the display device 67. The position/direction calculation unit 91 processes the sent induction signal, extracts a particular frequency signal having approximately the same frequency as the frequency of the position detection field M2 generated by the position detection signal generation unit 85 from the induction signal, and calculates the position and the direction of the capsule medical device 3 based on the extracted, particular frequency signal.

The magnetic-field/magnetization-direction angular-difference calculation unit 93 calculates the displacement (angle θ) between the field direction of the guidance field M1 at the position of the capsule medical device 3 and the magnetization direction of the permanent magnet 27.

The operating unit 95 allows an operator to indicate a travel direction and/or travel speed of the capsule medical device 3 based on an image of the inside of the body cavity and the position and the direction of the capsule medical device 3 displayed on the display device 67.

The guidance field generation unit 65 generates the guidance field M1 based on the information of the position and the direction of the capsule medical device 3 outputted from the external control unit 63. The guidance field generation unit 65 includes a guidance field control unit 97, a plurality of guidance coil drivers 99, and a plurality of guidance coils (field generation unit) 101.

The guidance field control unit 97 generates a control signal of the guidance field M1 based on an operation instruction signal from an operator and information that includes the position and the direction of the capsule medical device 3. The signal and information are outputted from the external control unit 63. The guidance field control unit 97 includes an operation information determination unit 103, a field/magnetization displacement determination unit (displacement detection unit) 105, a capsule direction displacement determination unit 107, and a generated-field calculation unit 109.

The operation information determination unit 103 detects an instruction signal based on the travel direction and the travel speed outputted by the operating unit 95.

The field/magnetization displacement determination unit 105 determines whether the value of the angle θ that is formed between the field direction of the guidance field M1 and the magnetization direction of the permanent magnet 27 and that is calculated by the magnetic-field/magnetization-direction angular-difference calculation unit 93 is equal to or less than a predetermined value or not.

The capsule direction displacement determination unit 107 determines whether the value of an angle α formed between the direction of the capsule medical device 3 as a control object and the detected current direction of the capsule medical device 3 is equal to or less than a predetermined value or not.

The generated-field calculation unit 109 calculates a guidance field M1 generated by the guidance coils 101.

According to a control signal from the guidance field control unit 97, the guidance coil driver 99 supplies a current to the guidance coils 101 so that the guidance coils 101 generate the guidance field M1.

The guidance coils 101 generate the guidance field M1 using the current supplied from the guidance coil driver 99.

Regarding the capsule medical device system 1 and the capsule medical device 3 configured in this way according to the embodiment, first the summary of operation is described, and then the features of the embodiment are described.

The capsule medical device system 1 according to the embodiment is used to acquire an image of the inside of the body cavity of a subject as follows. First, a subject is disposed in a space S to be subjected to a guidance field M1 formed by the guidance coils 101 arranged as shown in FIG. 1.

Next, each infrared sensor 59a in the capsule medical device 3 is exposed to infrared rays by an infrared generator (not shown), and the capsule medical device 3 is powered on. Then the capsule medical device 3 is put into a body cavity from the mouse or the anus of the subject. Moreover, in the external device 5, a power switch 111 of the extracorporeal device 61 is turned on by a battery 113 so that a power supply unit 115 is changed into an on-state. Thereby, power is supplied to each unit.

In the capsule medical device 3 put into the body cavity, operation of the imaging unit 9 is started after a predetermined time has passed, and an image of the inside of a body cavity illuminated by illumination light from the LED 37 is acquired by the image sensor 33. The acquired image signal is sent to the A/D converter control unit 45 via the control unit 25, then transferred to the radio transmitter 23 at a timing set by the timing generation circuit 49 based on the clock signal Clock and the vertical synchronizing signal V-Sync generated by the control unit 25 and then transmitted to the outside of the body via the radio transmitter 23.

The transmitted image signal is received by the radio receiver 69 via the antenna unit 81 provided in the extracorporeal device 61. The received image signal is inputted to the position detection field generation unit 79, and a trigger signal such as the vertical synchronizing signal V-Sync is detected therein. Then, the position detection signal generation unit 85 is started according to the detected trigger signal, and the signal generation coils 87 are thus excited, so that a position detection field M2 is generated in the space S in which the subject is disposed.

When the generated position detection field M2 is exerted on the capsule medical device 3, the position detection field M2 passes through the coil 17. Thereby an induction signal is induced in the coil 17. On the other hand, the position detection field M2 passes through even the magnetic sensor 13, and thus the magnetic sensor 13 outputs a detection signal based on the detected field intensity.

The induction signal and the detection signal are inputted to the field receiving unit 21 via the coil filter 19 and the sensor filter 15, respectively, and subjected to A/D conversion according to the timing set by the timing generation circuit 49, and then stored in the memory 51. Then, signals are transferred to the radio transmitter 23 via the multiplexer (mentioned as MUX in the relevant figure) 53, which is switched at the timing set by the timing generation circuit 49, and then transmitted to the outside of the body via the radio transmitter 23.

The transmitted induction signal and detection signal are received by the radio receiver 69 via the antenna unit 81 provided in the extracorporeal device 61. The received induction signal and detection signal are extracted and separated from the image signal by the data extraction unit 71. The separated induction signal and detection signal are directly sent to the external control unit 63. The image signal is subjected to compression processing in the image data compression unit 73 and then sent to the external control unit 63.

The induction signal, the detection signal, and the compressed image signal are synthesized in a mapped configuration to one another in the data synthesizing unit 75 and stored in the memory 77.

The image signal sent to the external control unit 63 is subjected to decompression processing in the image decompression processing unit 89 and then sent to the display device 67 to be displayed.

On the other hand, the induction signal sent to the external control unit 63 is sent to the position/direction calculation unit 91 and used for calculating the position and the direction of the capsule medical device 3. The detection signal sent to the external control unit 63 is sent to the magnetic-field/magnetization-direction angular-difference calculation unit 93 and used for calculating the angle formed between the magnetization direction of the permanent magnet 27 and a field direction of the guidance field M1 at the position of the capsule medical device 3.

The calculated position and direction of the capsule medical device 3 and the calculated angle formed between the magnetization direction of the permanent magnet 27 and the field direction of the guidance field M1 are sent to the display device 67 to be displayed, in addition, sent to the guidance field generation unit 65 and used for calculating a guidance field M1 to be generated.

When an operator confirms the image of the inside of the body cavity and the position and the direction of the capsule medical device 3, which are displayed on the display device 67, the operator operates the operating unit 95 of the external control unit 63 so as to input a travel direction and travel speed of the capsule medical device 3 into the guidance field generation unit 65. Based on the instruction signal on the travel direction and the travel speed inputted from the operating unit 95, and on the information of the position and the direction of the capsule medical device 3 inputted from the position/direction calculation unit 91, the guidance field generation unit 65 actuates the guidance coil drivers 99 so that the necessary intensity and direction of the guidance field M1 are achieved.

Thus, the guidance coils 101 are excited, so that a desired guidance field M1 is generated in the space S in which the subject exists.

When the guidance field M1 is exerted on the capsule medical device 3, the permanent magnet 27 disposed in the capsule medical device 3 generates drive force to rotate the capsule medical device 3 so that the magnetization direction of the magnet corresponds to the direction of the guidance field M1. When the guidance field M1 is generated in a direction inclined to the longitudinal axis R of the capsule medical device 3 with respect to the magnetization direction of the permanent magnet 27, drive force is generated such that the direction of the capsule medical device 3 is changed. On the other hand, when drive force is generated in a direction inclined to the circumferential direction of the capsule medical device 3 with respect to the magnetization direction of the permanent magnet 27, drive force is generated such that the capsule medical device 3 is rotated around the longitudinal axis R.

Since the spiral portion 29 is provided on the outer circumferential face of the package of the capsule medical device 3, when the capsule medical device 3 is rotated around the longitudinal axis R thereof due to the drive force, thrust is generated along the direction of the longitudinal axis R by an effect of the spiral portion 29. Thus, the capsule medical device 3 is propelled in the direction of the longitudinal axis R.

Next, description is made on a calculation method of the angle formed between the magnetization direction of the permanent magnet 27 and a field direction of the guidance field M1 at the position of the capsule medical device 3 and on the control method of the capsule medical device 3 based on the calculated angle, the methods being features of the embodiment.

Figure 7:
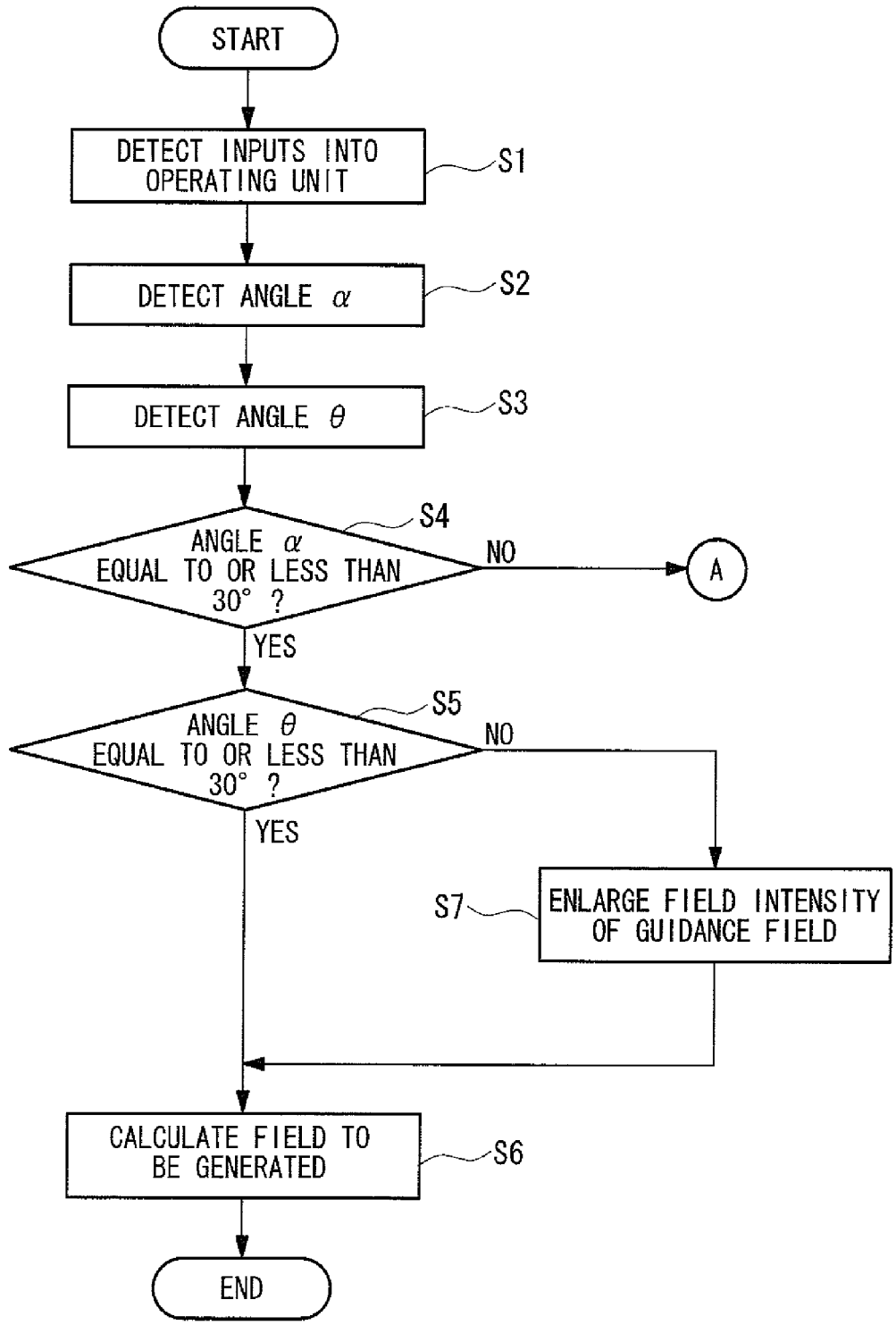
FIG. 7 is a flowchart for illustrating a control method of the capsule medical device in the capsule medical system of FIG. 1.

FIG. 7 shows a flowchart for illustrating a control method of the capsule medical device in the capsule medical system of FIG. 1.

An operator inputs a travel direction and travel speed of the capsule medical device 3 into the operating unit 95, and the operating unit 95 outputs an instruction signal based on the inputted travel direction and travel speed. The operation information determination unit 103 of the guidance field generation unit 65 detects the outputted instruction signal (step S1).

The instruction signal of the travel direction and travel speed detected by the operation information determination unit 103 is inputted to the generated-field calculation unit 109, and the generated-field calculation unit 109 calculates the direction of the capsule medical device 3, which is the direction of the longitudinal axis R, being a control object. The calculated direction of the capsule medical device 3 (control object) is inputted into the capsule direction displacement determination unit 107. On the other hand, the position and the direction of the capsule medical device 3 calculated by the position/direction calculation unit 91 are also inputted into the capsule direction displacement determination unit 107.

The capsule direction displacement determination unit 107 calculates the angle α that is formed between the direction of the capsule medical device 3 being the control object, and the detected, current direction of the capsule medical device 3 (step S2).

The magnetic-field/magnetization-direction angular-difference calculation unit 93 calculates the displacement (angle θ) between the field direction of the guidance field M1 at the position of the capsule medical device 3 and the magnetization direction of the permanent magnet 27 based on the intensity of the magnetic field detected by the magnetic sensor 13 and the field intensity of the guidance field M1 formed at the position of the capsule medical device 3.

Specifically, the magnetic-field/magnetization-direction angular-difference calculation unit 93 calculates the angle θ formed between the field direction of the guidance field M1 and the magnetization direction of the permanent magnet 27 according to the following formula (1).

$$BSENCE = Bint + Bext \cos \theta \quad (1)$$

Here, Bint shows the field intensity formed at the position of the medical device 1 by the permanent magnet 27. Bext shows the field intensity of the guidance field M1 at the position of the capsule medical device 3, and θ shows the angle formed between the direction of the sensitivity axis of the magnetic sensor 13 and the field direction of the guidance field M1. Therefore, Bext cos θ shows the field intensity component of the guidance field M1 detected by the magnetic sensor 13.

Bint is a predetermined, fixed value obtained by determining the relative positional relationship between the permanent magnet 27 and the magnetic sensor 13. Bext is a value obtained by determining the relative positional relationship between the capsule medical device 3 and the signal generation coils 87. Since the position of the capsule medical device 3 has been obtained by the position/direction calculation unit 91, Bext is an obtainable value.

Therefore, the magnetic-field/magnetization-direction angular-difference calculation unit 93 may calculate cos θ from formula (1), and obtain θ from cos θ.

When the angle α and the angle θ are calculated, the capsule direction displacement determination unit 107 determines whether the value of the angle α is equal to or less than the predetermined value (step S4).

When the value of the angle α is equal to or less than the predetermined value, the field/magnetization displacement determination unit 105 further determines whether the value of the angle θ is equal to or less than the predetermined value (step S5). Here, 30° may be exemplified as the predetermined value.

When either the angle α or the angle θ has a value equal to or less than the predetermined value, the generated-field calculation unit 109 calculates a guidance field M1 to be generated by the guidance coils 101 (step S6).

When the angle α has a value equal to or less than the predetermined value, and the angle θ has a value larger than the predetermined value, the generated-field calculation unit 109 sets the field intensity to be generated for a guidance field M1 to be large (step S7), and calculates the guidance field M1 (step S6).

Figure 8:
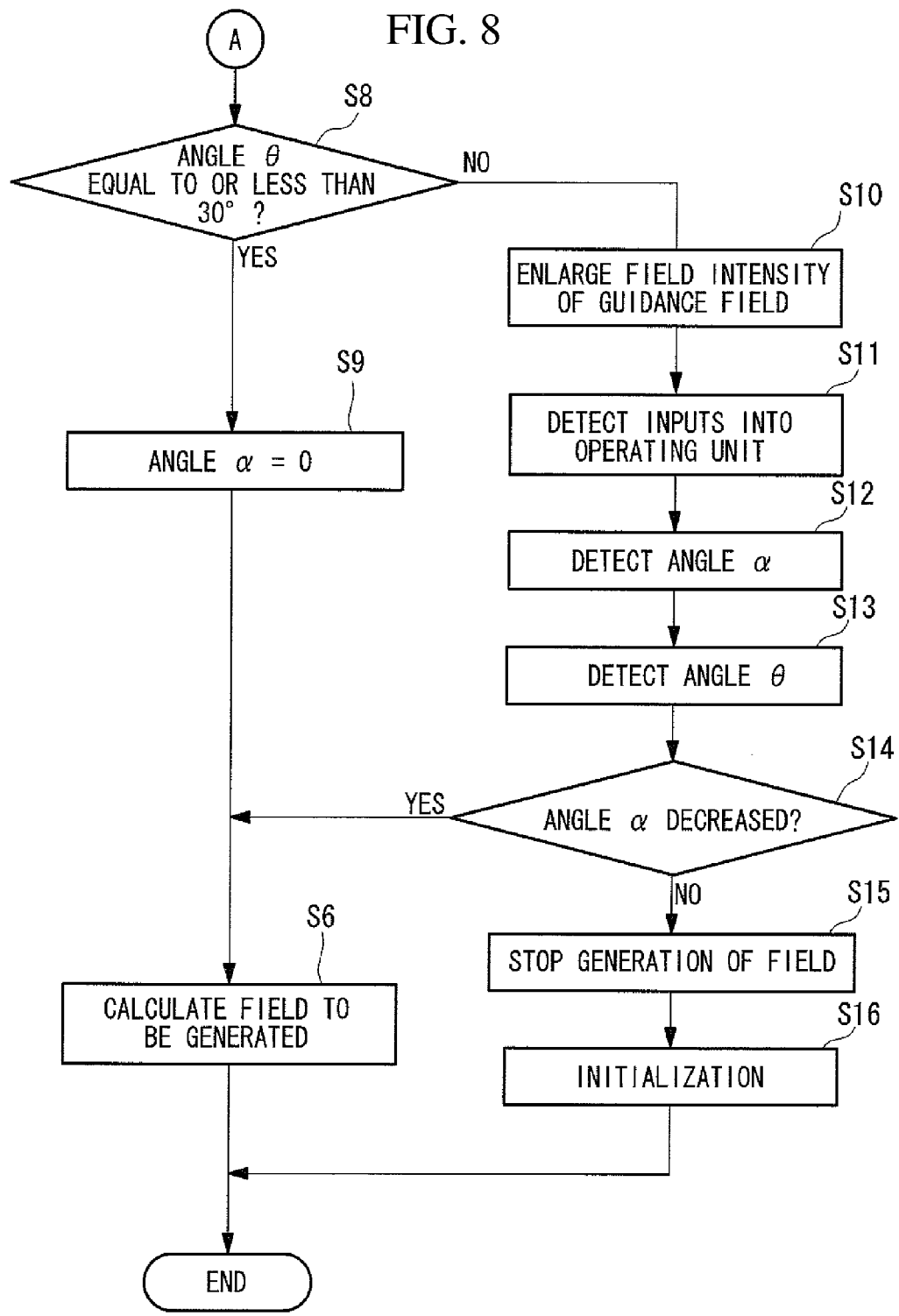
FIG. 8 is a flowchart for illustrating the control method of the capsule medical device in the capsule medical system of FIG. 1.

FIG. 8 shows a flowchart for illustrating the control method of the capsule medical device in the capsule medical system of FIG. 1.

When the value of the angle α is larger than the predetermined value, the field/magnetization displacement determination unit 105 further determines whether the value of the angle θ is equal to or less than the predetermined value as in step S5 (step S8).

When the angle α has a value larger than the predetermined value, and the angle θ has a value equal to or less than the predetermined value, the generated-field calculation unit 109 updates the direction information of the capsule medical device 3 set by the generated-field calculation unit 109 to the direction of the capsule medical device 3 detected by the position/direction calculation unit 91. That is, the generated-field calculation unit 109 assumes that the value of the angle α is 0 (step S9), and calculates a guidance field M1 to be generated by the guidance coils 101 (step S6).

When either the angle α or the angle θ has a value larger than the predetermined value and the angle θ has approximately the same value as the value of the angle α, the generated-field calculation unit 109 increases the field intensity to be generated for a guidance field M1 (step S10). Thus, torque exerted on the capsule medical device 3 can be increased.

Then, as in steps S1 to S3, input into the operating unit 95 is detected (step S11), the angle α is calculated (step S12), and the angle θ is calculated (step S13).

When the angle α is decreased compared with the value obtained in step S2, the generated-field calculation unit 109 continues control and calculates a guidance field M1 to be generated by the guidance coils 101 (step S14)

When the angle α is not decreased compared with the value obtained in step S2, the generated-field calculation unit 109 stops generation of the guidance field M1 (step S15) and initializes the respective parameters required for guiding the capsule medical device 3 (step S16).

After the parameters are initialized, the above control is repeated from step S1.

According to the above configuration, the field direction of the guidance field M1 is controlled based on the angle θ formed between the magnetization direction of the permanent magnet 27 and the field direction of the guidance field M1 applied to the permanent magnet 27 from the outside of a body. The angle θ induces attraction, torque, or the like to be exerted on the permanent magnet 27, so that the capsule medical device 3 is guided.

In this way, the field direction of the guidance field M1 is controlled based on the angle θ, which may prevent the phenomenon in which the capsule medical device 3 is unstably guided due to misalignment between the magnetization direction and the field direction. That is, the angle θ is controlled within a predetermined range (for example, within ±30°), which may prevent reduction in attraction for driving the capsule medical device 3 and reduction in torque for rotationally driving the capsule medical device 3. Consequently, the capsule medical device 3 is stably guided.

The attraction or torque exerted on the capsule medical device 3 is determined by the angle θ, the intensity of the guidance field M1, and the like. Therefore, the guidance field M1 is controlled so that the attraction or torque exerted on the capsule medical device 3 can be controlled. Consequently, the capsule medical device 3 can be stably guided.

The field direction of the guidance field M1 may be controlled based on not only the angle θ, but also the position and the direction of the capsule medical device 3. Since the permanent magnet 27 is provided in the capsule medical device 3, the position and the direction of the capsule medical device 3 can be easily converted into the position and the direction of the permanent magnet 27. Moreover, the field direction of guidance field M1 may be changed based on the positional relationship between the permanent magnet 27 and the guidance coils 101. Therefore, the field direction of the guidance field M1 is controlled based on the position of the capsule medical device, the direction of the capsule medical device, or both. Thereby the field direction of the guidance field M1 is appropriately controlled compared with a case in which control is not performed based on the position of the capsule medical device, the direction of the capsule medical device 3, or both, and consequently the capsule medical device 3 can be stably guided.

When the guidance field M1 is injected at a predetermined angle with respect to the sensitivity axis of the magnetic sensor 13, the magnetic sensor 13 outputs field intensity Bext cos θ, whose value is given by multiplying the intensity of the injected field Bext by the cosine of the angle. Therefore, when the detected field intensity BSENCE, and the field intensity Bext of the magnetic field formed at the position of the capsule medical device 3 are known, the angle θ formed between the direction of the magnetic field and the sensitivity axis may be calculated. Since the direction of the sensitivity axis of the magnetic sensor 13 and the magnetization direction of the magnet are in a predetermined, positional relationship, the magnetic-field/magnetization-direction angular-difference calculation unit 93 may calculate the angle θ formed between the magnetization direction of the magnet and the field direction of the guidance field M1.

As described in the embodiment, the field intensity of the guidance field M1 generated by the guidance coils 101 may be controlled. Alternatively, the following control may be performed for controlling the field intensity of the guidance field M1.

For example, in the case that the capsule medical device 3 is rotated around the longitudinal axis R, when rotation is continued, the field intensity of the guidance field M1 is set to be relatively low with respect to output from an input device. Thus, the field intensity to be generated for the guidance field M1 can be reduced, and reduced energy can be used for generating the guidance field M1.

When input from the input device is reduced, the field intensity of the guidance field M1 is increased. According to such control, displacement between the field direction of the guidance field M1 and the magnetization direction of the permanent magnet 27 in the capsule medical device 3 can be reduced. Thus, controllability of the capsule medical device 3 can be improved during low-speed rotation.

Furthermore, when rotation of the guidance field M1 is stopped, the following operation is performed: the field intensity of the guidance field M1 is temporarily increased, and after the rotation of the capsule medical device 3 has been stopped, the field intensity of the guidance field M1 is decreased. According to such operation, the motion of the capsule medical device 3 can be stopped while the magnetization direction of the permanent magnet 27 provided in the capsule medical device 3 is made to substantially correspond to the field direction of the guidance field M1 formed by the guidance coils 101. Therefore, controllability can be improved when the capsule medical device 3 is operated again.

Furthermore, when the operation for changing the direction of the capsule medical device 3 is performed, the same effect can be obtained by performing the same control.

First Modification of First Embodiment

Next, a first modification of the first embodiment of the invention is described with reference to FIGS. 9 to 11.

The basic configuration of the capsule medical device system of the modification is the same as that of the first embodiment. However, the system is different from the first embodiment in the detection method of the magnetization direction of the permanent magnet mounted in the capsule medical device. Therefore, in the modification, only particulars regarding the detection method of the guidance field M1 are described with reference to FIGS. 9 to 11, and description of other components and the like are omitted.

Figure 9:
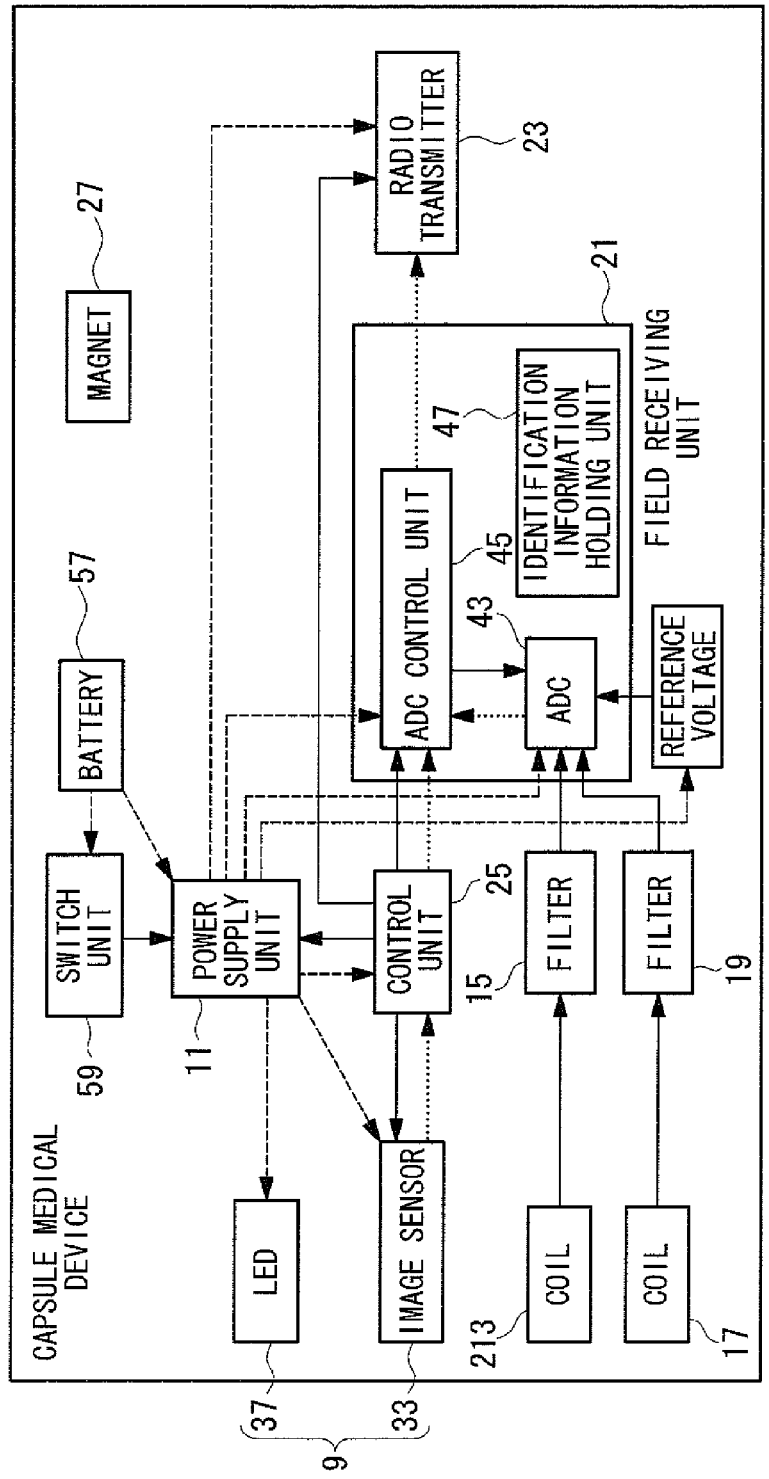
FIG. 9 is a block diagram showing a capsule medical device according to a first modification of the first embodiment of the invention.
Figure 10:
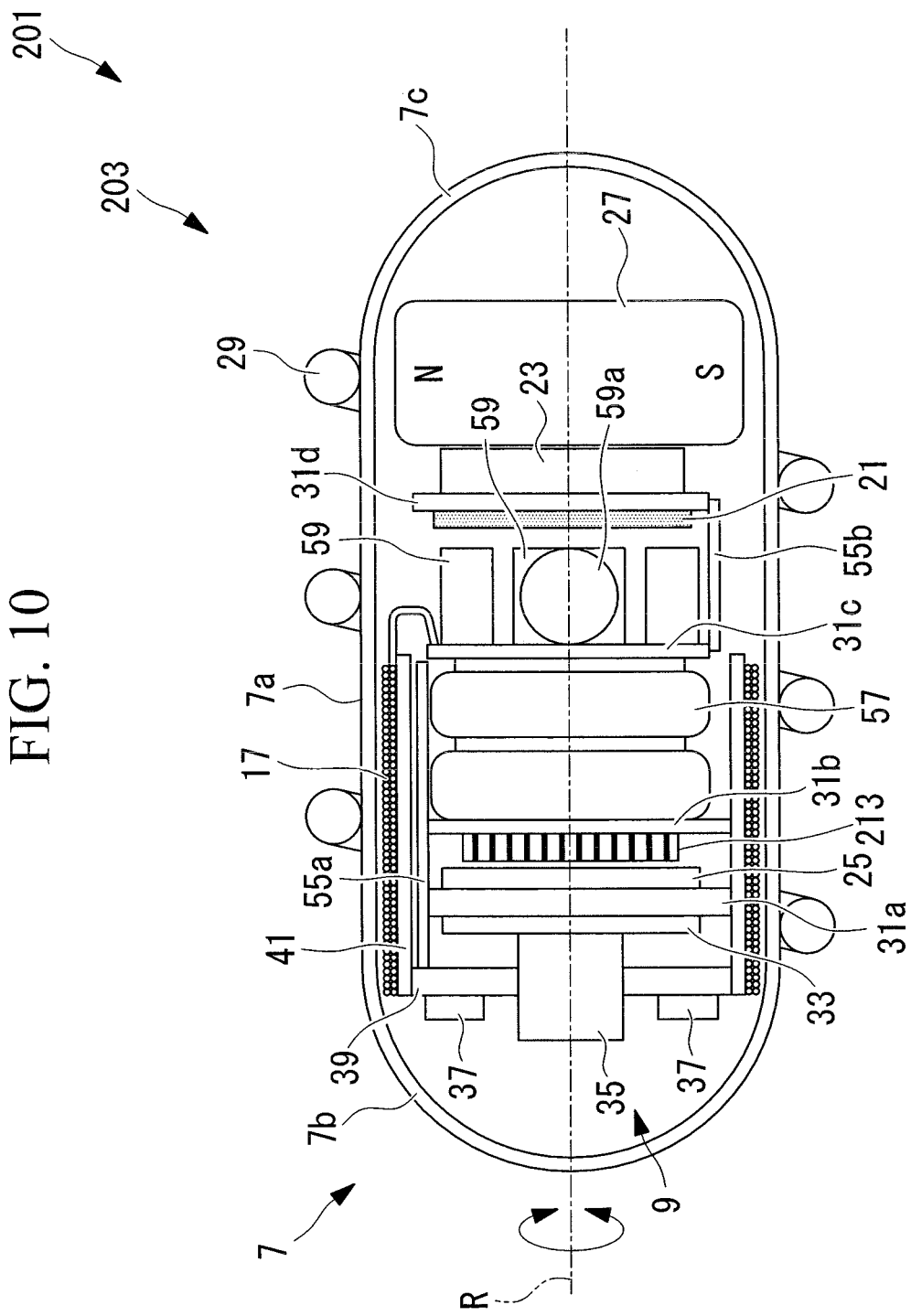
FIG. 10 is a longitudinal section view showing the capsule medical device of FIG. 9.

FIG. 9 shows a block diagram of a capsule medical device according to the modification, and FIG. 10 shows a longitudinal section view of the capsule medical device of FIG. 9.

The same components as in the first embodiment are marked with the same symbols, and descriptions of them are omitted.

As shown in FIGS. 9 and 10, the capsule medical device (medical device) 203) in the capsule medical device system (medical guidance system) 201 of the modification includes a package 7, an imaging unit 9, a power supply unit 11, a magnetization direction detection coil (alternating field detection unit) 213, a sensor filter 15 that filters a detection signal from the magnetization direction detection coil 213, a coil 17, a coil filter 19, a field receiving unit 21 that processes an induction signal and a detection signal, a radio transmitter 23, a control unit 25, and a permanent magnet 27.

As the magnetic sensor 13 in the first embodiment, the magnetization direction detection coil 213 detects a magnetic field that has a field direction along the magnetization direction of the permanent magnet 27.

Figure 11:
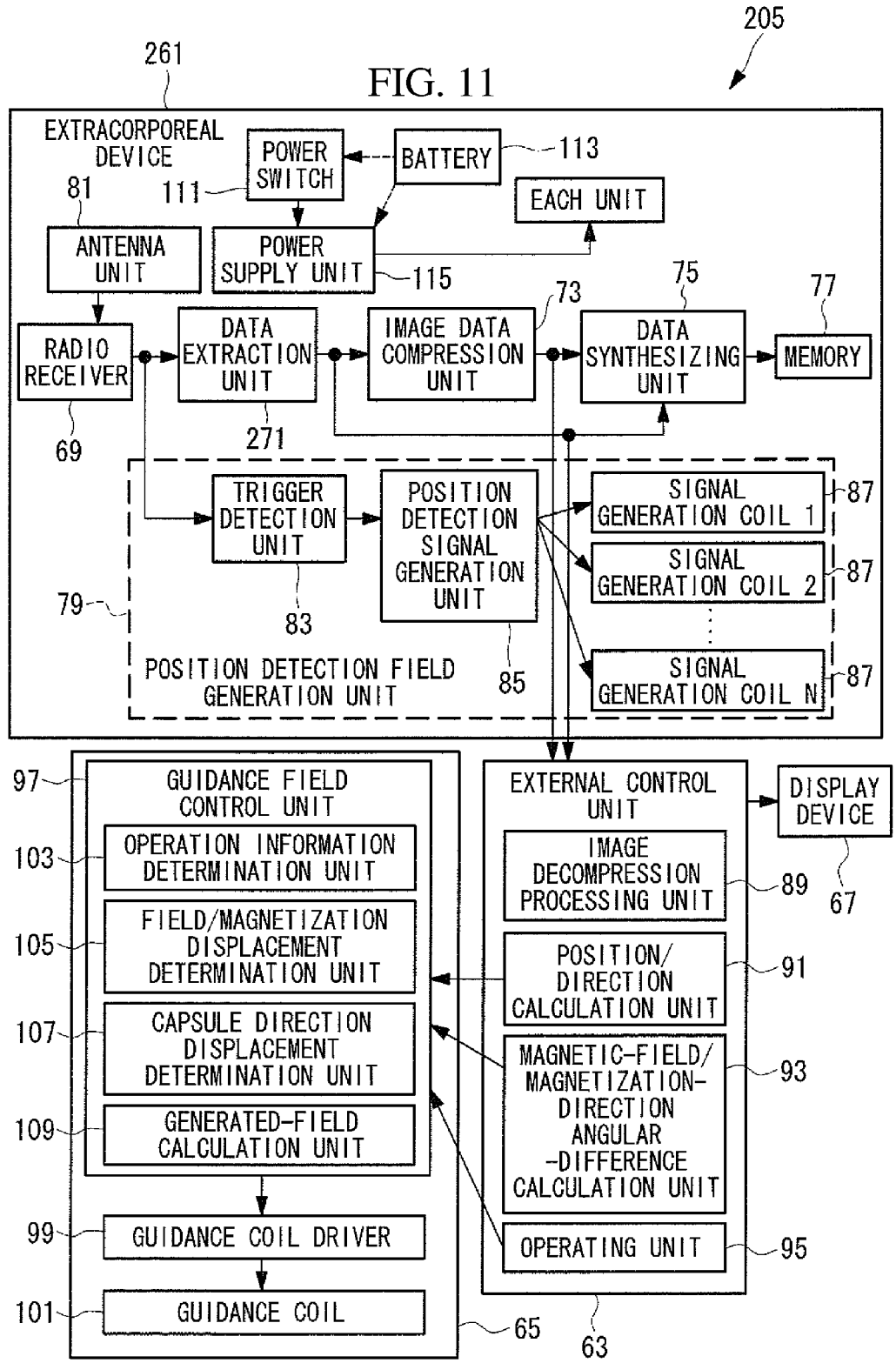
FIG. 11 is a block diagram showing an external device in a capsule medical device system according to the first modification of the first embodiment of the invention.

FIG. 11 shows a block diagram of an external device in the capsule medical device system according to the modification.

As shown in FIG. 11, the external device 205 includes an extracorporeal device 261 that generates a magnetic field M2 for position detection, an external control unit 63 that calculates the position and the direction of the capsule medical device 203, a guidance field generation unit 65 that generates a magnetic field M1 for guidance, and a display device 67 that displays an image based on an image signal outputted from the external control unit 63.

The extracorporeal device 261 receives a signal sent from the capsule medical device 203, and generates position detection field M2. The extracorporeal device 261 includes a radio receiver 69, a data extraction unit 271, an image data compression unit 73, a data synthesizing unit 75, a memory 77, and a position detection field generation unit (alternating field generation unit) 79.

The data extraction unit 271 extracts the induction signal and the detection signal generated by their respective coils from signals received by the radio receiver 69. The signals received by the radio receiver 69 include an image signal, the induction signal, and the detection signal. Since the image signal has a predetermined length, the data extraction unit 271 can easily separate the image signal from the induction signal and detection signal that follow the image signal.

In the capsule medical device system 201 and the capsule medical device 203 configured in this way according to the modification, the calculation method of the angle formed between the magnetization direction of the permanent magnet 27 and the field direction of the guidance field M1 at the position of the capsule medical device 203 is different from the calculation method in the first embodiment only in that the angle is calculated using the field intensity detected by the magnetization direction detection coil 213. Since other operations are the same as in the first embodiment, description of the operations is omitted.

According to the above configuration, when the guidance field M1, which is an alternating field, is injected at a predetermined angle with respect to the sensitivity axis, the magnetization direction detection coil 213 outputs field intensity whose value is given by multiplying the intensity of the injected field by the cosine of the angle. Therefore, when the detected field intensity and the field intensity of the guidance field M1 formed at the position of the capsule medical device 203 are known, the angle formed between the direction of the magnetic field and the sensitivity axis may be calculated. Since the direction of the sensitivity axis of the magnetization direction detection coil 213 and the magnetization direction of the permanent magnet 27 are in a predetermined, positional relationship, the magnetic-field/magnetization-direction angular-difference calculation unit 93 may calculate an angle θ formed between the magnetization direction of the permanent magnet 27 and the field direction of the guidance field M1.

Second Modification of First Embodiment

Next, a second modification of the first embodiment of the invention is described with reference to FIG. 12.

The basic configuration of the capsule medical device system of the modification is the same as that of the first modification. However, the system is different from the first modification in magnetic field detected by a magnetization direction detection coil. Therefore, in the modification, only the detection method of the magnetization direction of the permanent magnet mounted in the capsule medical device is described using FIG. 12, and descriptions of other components and the like are omitted.

Figure 12:
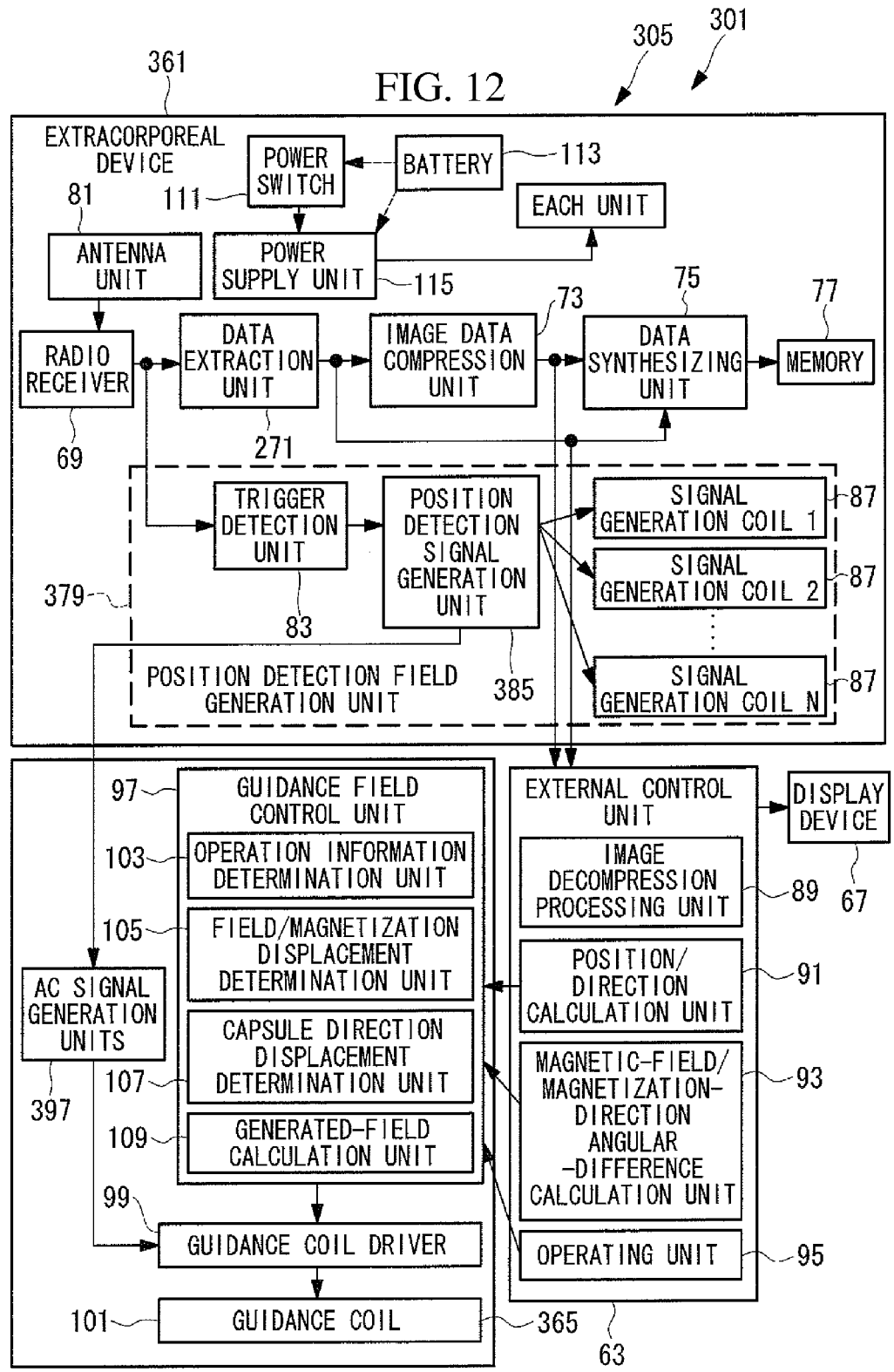
FIG. 12 is a block diagram showing an external device in a capsule medical device system according to a second modification of the first embodiment of the invention.

FIG. 12 shows a block diagram of an external device in a capsule medical device system according to the modification.

The same components as in the first modification of the first embodiment are marked with the same symbols, and descriptions of them are omitted.

As shown in FIG. 12, an external device 305 in a capsule medical device system (medical guidance system) 301 according to the modification includes an extracorporeal device 361 that generates a magnetic field M2 for position detection, an external control unit 63 that calculates the position and the direction of the capsule medical device 203, a guidance field generation unit 365 that generates a magnetic field M1 for guidance, and a display device 67 that displays an image based on an image signal outputted from the external control unit 63.

The extracorporeal device 361 receives a signal sent from the capsule medical device 203, and generates the position detection field M2. The extracorporeal device 361 includes a radio receiver 69, a data extraction unit 271, an image data compression unit 73, a data synthesizing unit 75, a memory 77, and a position detection field generation unit 379.

The position detection field generation unit 379 includes a trigger detection unit 83 that detects a trigger signal included in image information, a position detection signal generation unit 385 that outputs a position detection signal and outputs a signal for detecting the magnetization direction of the permanent magnet 27 mounted in the capsule medical device, and a plurality of signal generation coils 87 that generate the position detection field M2.

The guidance field generation unit 365 generates the guidance field M1 based on information of the position and the direction of the capsule medical device 203 outputted from the external control unit 63. The guidance field generation unit 365 includes a guidance field control unit 97, a plurality of AC signal generation units 397, a plurality of guidance coil drivers 99, and a plurality of guidance coils (alternating field generation unit) 101 forming a Helmholtz coil.

According to a signal from the position detection signal generation unit 385, the AC signal generation units 397 allow the guidance coils 101 to generate the guidance field M1, which is used for detecting the magnetization direction of the permanent magnet 27.

In the calculation of the angle formed between the magnetization direction of the permanent magnet 27 and the field direction of the guidance field M1 at the position of the capsule medical device 203, operation of the guidance field generation unit 365 configured in this way is described.

The position detection signal generation unit 385 allows the guidance coils 101 to generate an AC signal (1 kHz or more) in a manner of being superimposed with the guidance field M1 at a timing different from the timing at which the position detection field M2 is generated by the signal generation coils 87. Since the guidance coils 101 have the configuration of a triaxial Helmholtz coil that generates a magnetic field in triaxial different directions respectively, the guidance coils form a uniform, parallel magnetic field regardless of a place.

In this way, the guidance field M1 can be formed as a uniform, parallel magnetic field. Therefore, the direction of the magnetization direction detection coil 213 can be more securely detected, and the magnetization direction of the permanent magnet 27 can be detected.

In the capsule medical device system 301 according to the modification, the calculation method of the angle formed between the magnetization direction of the permanent magnet 27 and the field direction of the guidance field M1 at the position of the capsule medical device 203 and the control method of the capsule medical device 203 based on the calculated angle are the same as in the first modification, therefore descriptions of each method are omitted.

According to the above configuration, the magnetization direction of the permanent magnet 27 is calculated based on alternating field information detected by the magnetization direction detection coil 213. Since the calculated magnetization direction approximately corresponds to the magnetization direction of the permanent magnet 27, the magnetic-field/magnetization-direction angular-difference calculation unit 93 may calculate the angle θ based on the calculated magnetization direction.

Third Modification of First Embodiment

Next, a third modification of the first embodiment of the invention is described with reference to FIGS. 13 and 14.

The basic configuration of the capsule medical device system of the modification is the same as that of the second modification of the first embodiment. However, the system is different from the second modification of the first embodiment in magnetic field detected by a magnetization direction detection coil. Therefore, in the modification, only the detection method of the magnetization direction of the permanent magnet mounted in the capsule medical device is described using FIGS. 13 and 14, and descriptions of other components and the like are omitted.

Figure 13:
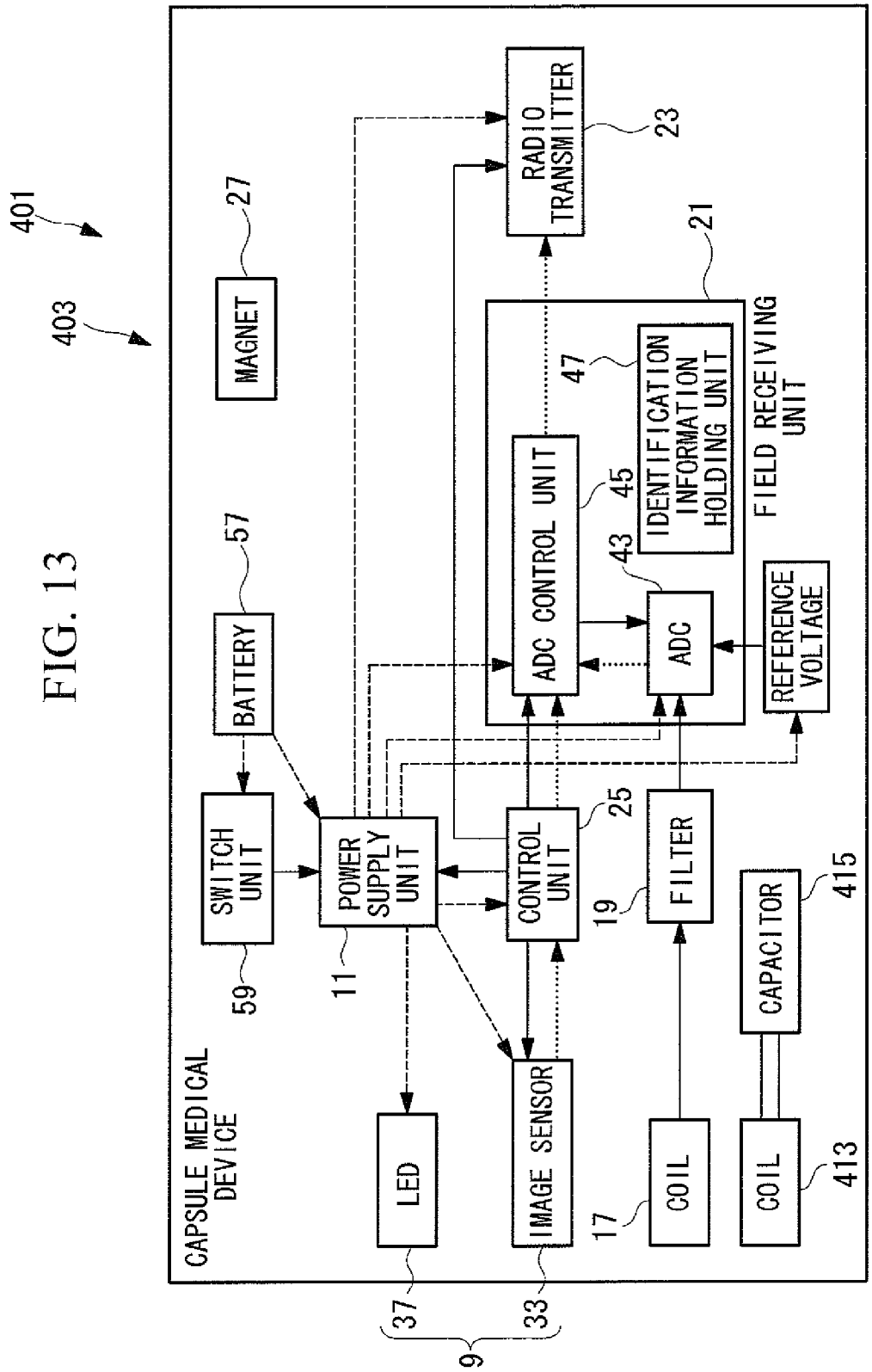
FIG. 13 shows a block diagram of a capsule medical device in a capsule medical device system according to a third modification of the first embodiment of the invention.

FIG. 13 shows a block diagram of a capsule medical device in a capsule medical device system according to the modification.

The same components as in the first modification of the first embodiment are marked with the same symbols, and descriptions of them are omitted.

As shown in FIG. 13, a capsule medical device (medical device) 403 in a capsule medical device system (medical guidance system) 401 of the modification includes a package 7, an imaging unit 9, a power supply unit 11, a magnetization direction detection coil 413, a capacitor 415 forming an LC resonance circuit with the magnetization direction detection coil 413, a coil 17, a coil filter 19, a field receiving unit 21 that processes an induction signal and a detection signal, a radio transmitter 23, a control unit 25, and a permanent magnet 27.

As the magnetic sensor 13 in the first embodiment, the magnetization direction detection coil 413 detects a magnetic field having a field direction along the magnetization direction of the permanent magnet 27. The magnetization direction detection coil 413 and the capacitor 415 form the LC resonance circuit, which resonates with a magnetic field having the same frequency as the resonance frequency.

Figure 14:
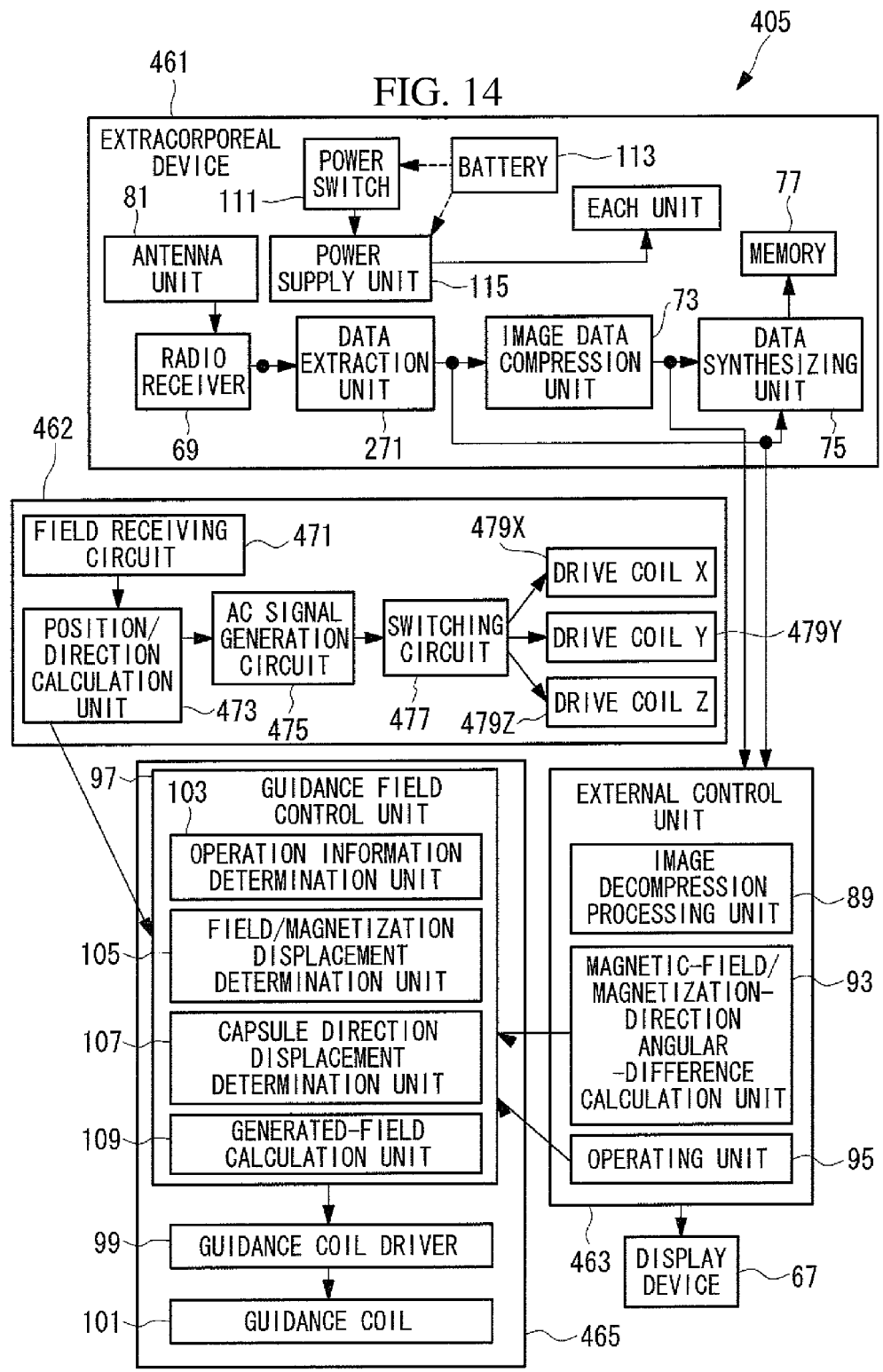
FIG. 14 shows a block diagram of an external device in the capsule medical device system according to the third modification of the first embodiment of the invention.

FIG. 14 shows a block diagram of an external device in the capsule medical device system according to the modification.

As shown in FIG. 14, the external device 405 includes an extracorporeal device 461 that receives a signal sent from the capsule medical device 403 and transmits data required for calculating the position and the direction of the capsule medical device to an external control unit 463, a position detection unit 462 that detects the position and the direction of the capsule medical device 403, the external control unit 463 that calculates the position and the direction of the capsule medical device 403, a guidance field generation unit 465 that generates a magnetic field M1 for guidance, and a display device 67 that displays an image based on an image signal outputted from the external control unit 463.

The extracorporeal device 461 includes a radio receiver 69, a data extraction unit 271, an image data compression unit 73, a data synthesizing unit 75, and a memory 77.

The position detection unit 462 includes a plurality of field receiving circuits 471, a position/direction calculation unit 473, an AC signal generation circuit 475, a switching circuit 477, and a plurality of drive coils 479X, 479Y and 479Z.

The field receiving circuit 471 detects an alternating field for position detection M3 that is generated by drive coils 479X, 479Y and 479Z, and a resonance field M4 that is generated by a magnetization direction detection coil 413. The respective field receiving circuits 471 are disposed in the periphery of the working area of the capsule medical device 403.

The position/direction calculation unit 473 calculates the magnetization direction of the permanent magnet 27 and outputs an instruction signal for generating the alternating field M3. Specifically, the position/direction calculation unit 473 extracts a signal on the resonance field M4 from a detection signal inputted from the field receiving circuits 471, and calculates the coil axis direction of the magnetization direction detection coil 413, namely, the magnetization direction of the permanent magnet 27.

The position/direction calculation unit 473 calculates the position and the direction of the capsule medical device 403 based on the detection signal on the resonance field from the coil 17. Here, five values except a phase around the longitudinal axis R are calculated.

The AC signal generation circuit 475 generates, for example, an AC signal having the resonance frequency of the LC resonance circuit according to an instruction signal inputted from the position/direction calculation unit 473.

The switching circuit 477 inputs the AC signal into a predetermined coil from among drive coils 479X, 479Y, and 479Z according to an instruction signal inputted from the position/direction calculation unit 473.

Drive coil 479X, 479Y, or 479Z generates an alternating field M3 for position detection that has the same frequency as the resonance frequency of the LC resonance circuit according to the inputted AC signal. The drive coils 479X, 479Y, and 479Z have a Helmholtz coil configuration, and the three drive coils 479X, 479Y, and 479Z configure a triaxial Helmholtz coil.

For the capsule medical device system 401 configured in this way according to the modification, description is made on a calculation method of the angle formed between the magnetization direction of the permanent magnet 27 and the field direction of the guidance field M1 at the position of the capsule medical device 403 and on the control method of the capsule medical device 403 based on the calculated angle. Since the summaries of operation of both the capsule medical device system 401 and the capsule medical device 403 are the same as in the first modification, descriptions of the operations are omitted.

The position detection unit 462 outputs an instruction signal instructing generation of the alternating field M3 for position detection to the AC signal generation circuit 475. The AC signal generation circuit 475 generates an AC signal according to the instruction signal and outputs the AC signal to the switching circuit 477. The switching circuit 477 inputs the AC signal into a predetermined drive coil 479X, 479Y or 479Z according to the instruction signal. The drive coil 479X, 479Y, or 479Z forms the alternating field M3 for position detection in the working area of the capsule medical device 403 according to the inputted AC signal.

Resonance occurs in the LC resonance circuit in the capsule medical device 403. The LC resonance circuit includes the magnetization direction detection coil 413 and the capacitor 415, thereby the LC resonance circuit generates the resonance field M4.

The field receiving circuit 471 detects the alternating field M3 for position detection and the resonance field M4 and outputs a detection signal to the position/direction calculation unit 473. The position/direction calculation unit 473 extracts a signal on the resonance field M4 from the detection signal and calculates the magnetization direction of the permanent magnet 27 from the signal on the resonance field M4. The calculated magnetization direction of the permanent magnet 27 is outputted to the guidance field generation unit 465.

Since the calculation method of the magnetization direction of the permanent magnet 27 is the same as in the first embodiment, the description of the method is omitted.

Since the method of calculating the angle to be formed in the guidance field generation unit 465 is the same as in the first embodiment, the description of the method is omitted.

According to the above configuration, an external coil need not be additionally provided for detecting the magnetization direction of the permanent magnet 27 in the capsule medical device 403. Since a simple algorithm may be used to obtain the magnetization direction of the permanent magnet 27, the capsule medical device 403 can be efficiently controlled.

Second Embodiment

Next, a second embodiment of the invention is described with reference to FIGS. 15 to 18.

The basic configuration of the capsule medical device system of the embodiment is the same as that of the first embodiment, but different from the first embodiment in method of detection of the magnetization direction of the permanent magnet mounted in the capsule medical device. Therefore, in the embodiment, only the method of detection of the magnetization direction of the permanent magnet is described using FIGS. 15 to 18, and descriptions of other components and the like are omitted.

Figure 15:
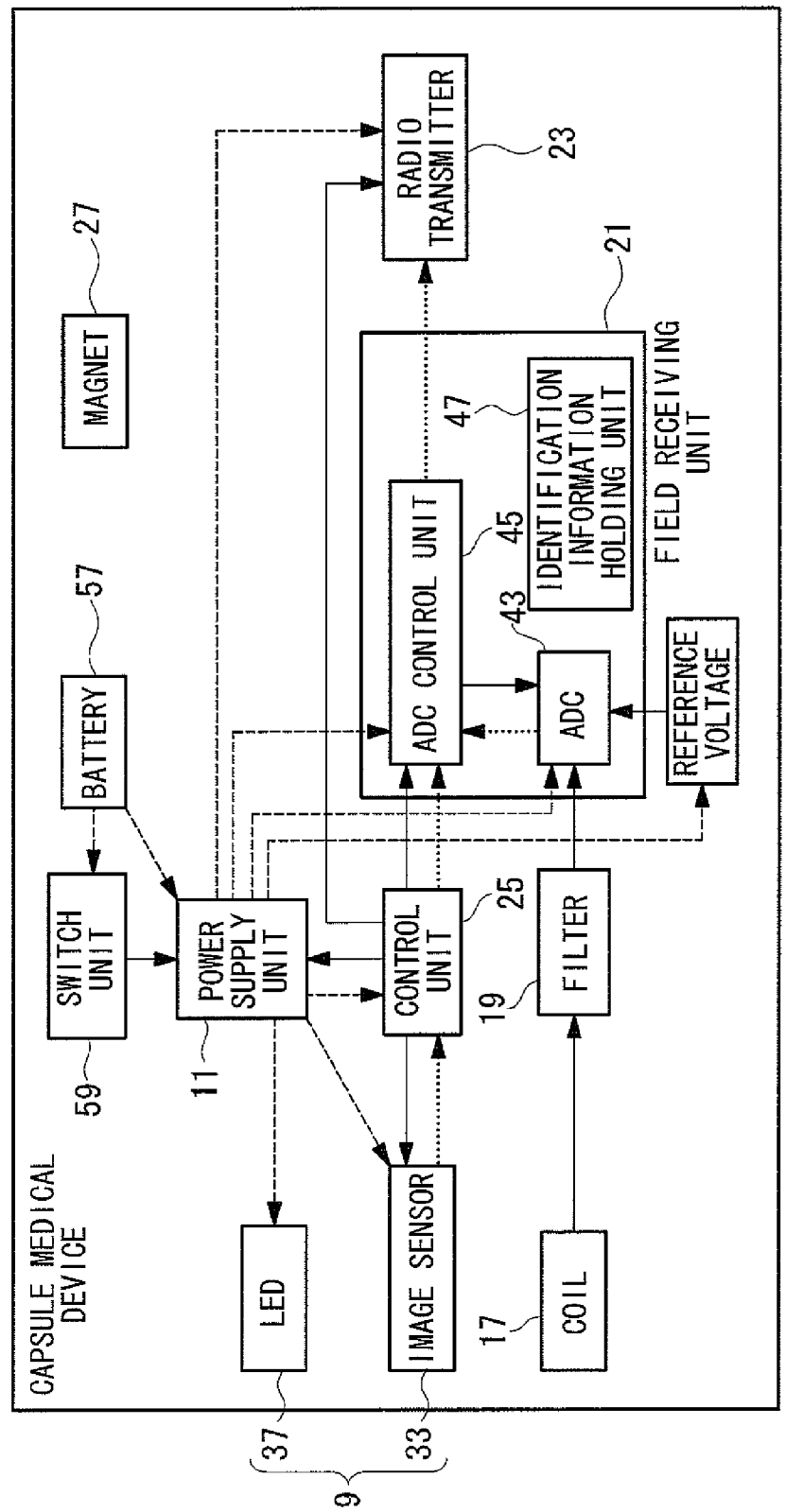
FIG. 15 shows a block diagram of a capsule medical device according to a second embodiment of the invention.

FIG. 15 shows a block diagram of the capsule medical device according to the embodiment.

The same components as in the first embodiment are marked with the same symbols, and descriptions of them are omitted.

As shown in FIG. 15, a capsule medical device (medical device) 503 in a capsule medical device system (medical guidance system) 501 includes a package 7, an imaging unit 9, a power supply unit 11, a coil 17, a coil filter 19, a field receiving unit 21, a radio transmitter 23, a control unit 25, and a permanent magnet 27.

Figure 16:
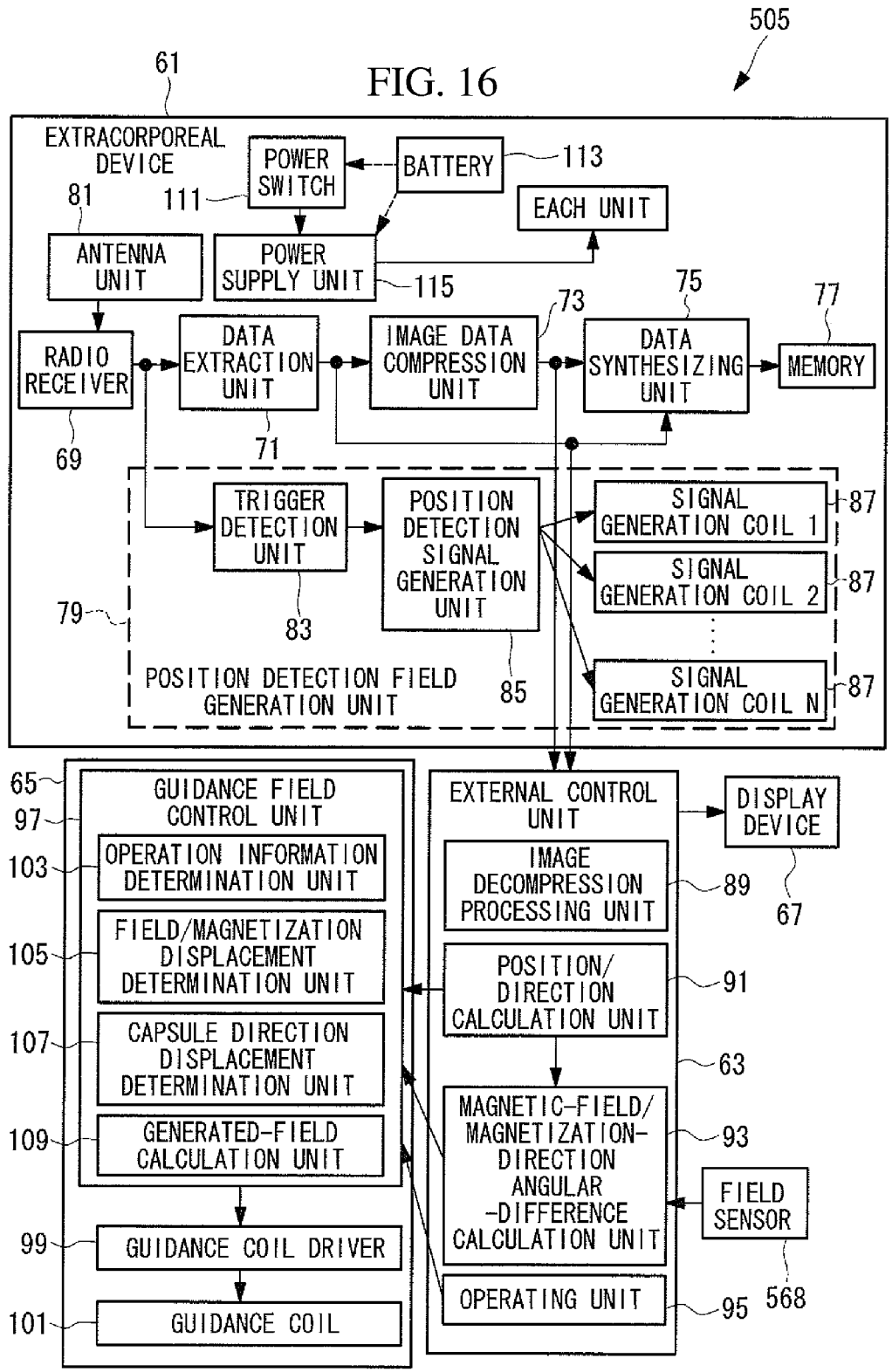
FIG. 16 shows a block diagram of an external device in the capsule medical device system according to the second embodiment of the invention.

FIG. 16 shows a block diagram of an external device in the capsule medical device system according to the embodiment.

As shown in FIG. 16, the external device 505 includes an extracorporeal device 61 that generates a magnetic field M2 for position detection, an external control unit 63 that calculates the position and the direction of the capsule medical device 503, a guidance field generation unit 65 that generates a magnetic field M1 for guidance, a display device 67 that displays an image based on an image signal outputted from the external control unit 63, and field sensors (external field detection unit) 568 that detect the magnetization direction of the permanent magnet 27 in the capsule medical device 503.

The field sensors 568 detect the field intensity of the permanent magnet 27 and the field intensity of the guidance field M1 and are disposed in the periphery of the working area of the capsule medical device 503.

A plurality of field sensors 568 may be disposed in the periphery of the working area of the capsule medical device 503 as described above. Alternatively, a single triaxial field sensor 568 may be used without being particularly limited to this.

For the external device 505 configured in this way, description is made on a calculation method of the angle formed between the magnetization direction of the permanent magnet 27 and the field direction of the guidance field M1 at the position of the capsule medical device 503.

Figure 17:
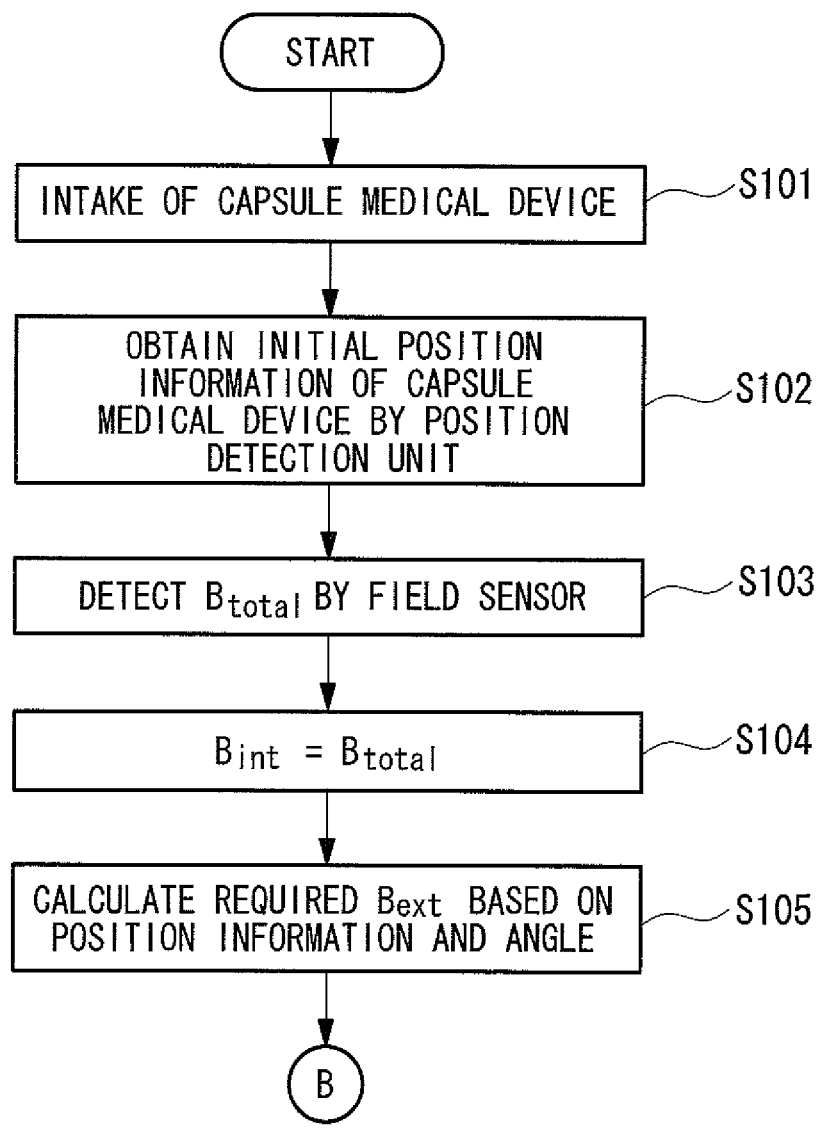
FIG. 17 is a flowchart for illustrating the calculation method of the angle formed between the magnetization direction and the field direction in the second embodiment of the invention.

FIG. 17 shows a flowchart for illustrating the calculation method of the angle formed between the magnetization direction and the field direction in the embodiment.

First, the capsule medical device 503 is powered on, and then the capsule medical device 503 is put into a body cavity from the mouth or the anus of a subject (step S101).

Then, the external device 505 acquires the position and the direction (initial position information) of the capsule medical device 503 (step S102). Since the detection method of the position of the capsule medical device 503 and the like is the same as in the first embodiment, the description of the method is omitted.

When the capsule medical device 503 is disposed in the working area, the field sensors 568 detect a magnetic field (Btotal) expressed by the following formula (2) and outputs a detection signal based on the intensity of the magnetic field (Btotal; step S103).

$$Btotal = Bint + Bext \quad (2)$$

Here, Bint shows the intensity of a magnetic field formed by the permanent magnet 27, and Bext shows the field intensity of the guidance field M1 formed by the guidance coils 101.

An output signal from the field sensors 568 is inputted to the magnetic-field/magnetization-direction angular-difference calculation unit 93 of the external control unit 63, in which the magnetic field (Bint) formed by the permanent magnet 27 is calculated (step S104). In this stage, the guidance coils 101 do not generate the guidance field M1. Therefore, Bext=0 is established, and formula (2) can be expressed as Bint=Btotal.

Then, as in the first embodiment, the magnetic-field/magnetization-direction angular-difference calculation unit 93 calculates an angle θ formed between the magnetization direction of the permanent magnet 27 and the field direction of the guidance field M1 at the position of the capsule medical device 503.

The calculated angle θ is outputted to the guidance field generation unit 65 in the same way as acquired information such as the position of the capsule medical device 503.

The generated-field calculation unit 109 of the guidance field generation unit 65 calculates the required magnetic field Bext of a guidance field M1 based on inputted information such as the position and the angle θ (step S105).

Figure 18:
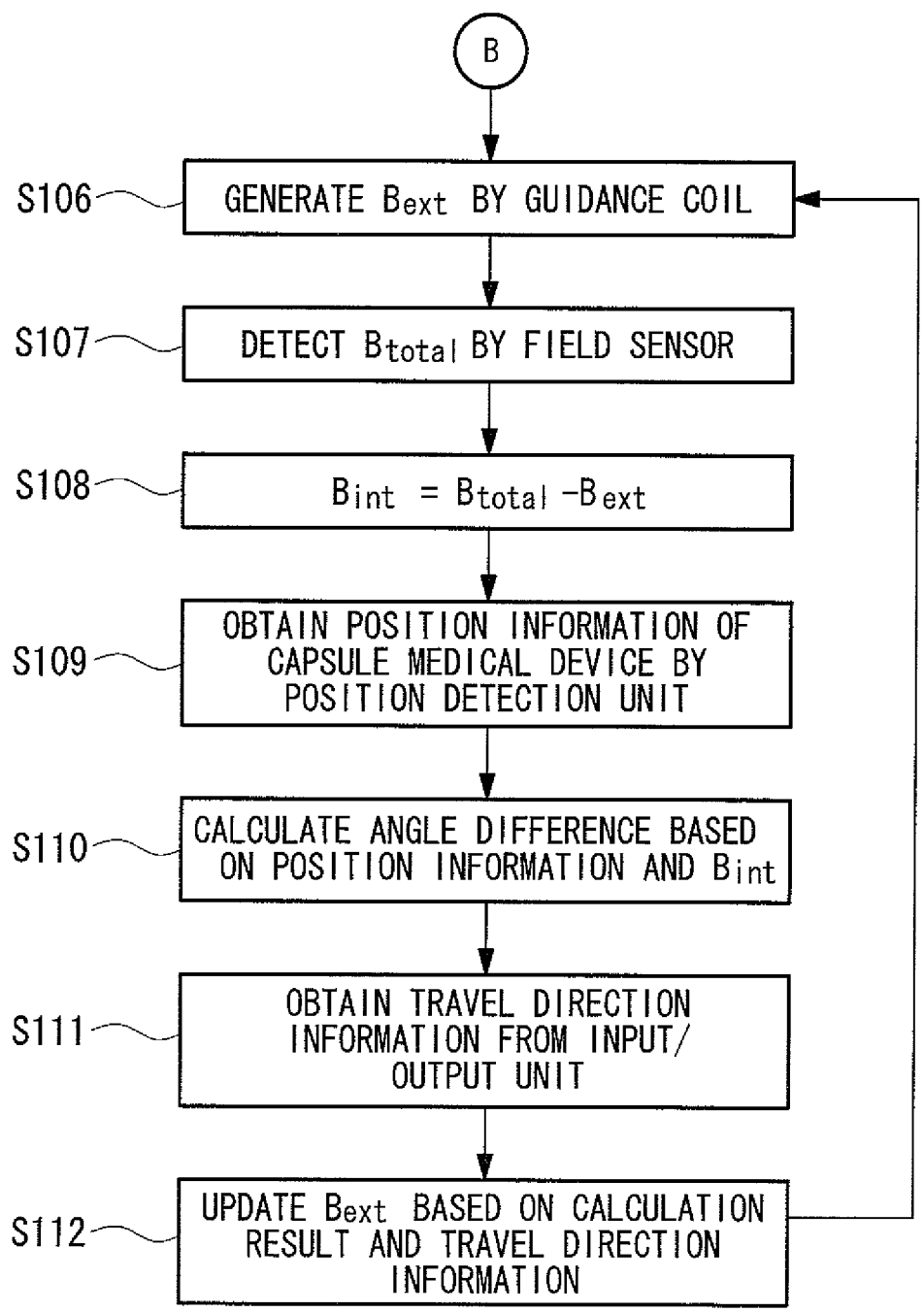
FIG. 18 is a flowchart for illustrating control of a magnetic field applied from guidance coils based on the calculated angle θ.

FIG. 18 shows a flowchart for illustrating control of a magnetic field generated by the guidance coils based on the calculated angle θ.

The generated-field calculation unit 109 outputs an instruction signal for generating a guidance field M1 equal to calculated magnetic field Bext to the guidance coil drivers 99 so that the guidance coils 101 generate the guidance field M1 (step S106).

Then, the field sensors 568 detect the magnetic field (Btotal) formed at the position of the field sensors 568 (step S107).

A detection signal from the field sensors 568 is inputted to the magnetic-field/magnetization-direction angular-difference calculation unit 93, and the magnetic field (Bint) formed by the permanent magnet 27 is obtained according to the following formula (3) (step S108).

$$Bint = Btotal - Bext \quad (3)$$

Then, the external device 505 acquires the position and the direction (initial position information) of the capsule medical device 503 again (step S109).

The magnetic-field/magnetization-direction angular-difference calculation unit 93 calculates the angle θ formed between the magnetization direction of the permanent magnet 27 and the field direction of the guidance field M1 at the position of the capsule medical device 503 based on information such as the magnetic field (Bint) calculated in step S108 and the information of the position of the capsule medical device 503 acquired in step S109 (step S110).

Then, information inputted into the operating unit 95, including the travel direction and travel speed of the capsule medical device 503, are outputted to the capsule direction displacement determination unit 107 (step S111).

The capsule direction displacement determination unit 107 calculates an angle α formed between the travel direction (control object direction) of the capsule medical device 503 and the direction of the longitudinal axis R of the capsule medical device 503 based on the inputted information, such as the travel direction of the capsule medical device 503 and the information of the position and direction of the capsule medical device 503. The generated-field calculation unit 109 calculates the required magnetic field Bext of a guidance field M1 based on the calculated angle α and the inputted information, such as the travel direction of the capsule medical device 503, and updates the magnetic field Bext value (step S112).

The generated-field calculation unit 109 allows the guidance coils 101 to generate a guidance field M1 based on the updated magnetic field Bext value (step S106).

Thereafter, the above control is repeated.

According to the above configuration, the magnetization direction of the permanent magnet 27 in the capsule medical device 503 is detected. Thereby the displacement (angle θ) between the guidance field M1 at the capsule medical device 503 and the magnetization direction of the permanent magnet 27 can be corrected. As a result, the guidance field M1 and the internal permanent magnet 27 can be optimally set respectively. Therefore, power consumption of the guidance field generation unit 65 can be suppressed, and the permanent magnet 27 within the capsule medical device 503 can be reduced in size. In addition, the capsule medical device 503 can be stably controlled.

The magnetic field formed in the periphery of the capsule medical device 503 by the permanent magnet 27 is detected by the field sensors 568, and the magnetization direction of the permanent magnet 27 is calculated based on the detected field information. Since the calculated magnetization direction approximately corresponds to the magnetization direction of the permanent magnet 27, the magnetic-field/magnetization-direction angular-difference calculation unit 93 may calculate the angle θ based on the calculated magnetization direction.

Modification of Second Embodiment

Next, a modification of the second embodiment of the invention is described with reference to FIGS. 19 to 21.

The basic configuration of the capsule medical device system of the modification is the same as that of the second embodiment, but different from the second embodiment in the method of detection of the magnetization direction of the permanent magnet mounted in the capsule medical device. Therefore, in the modification, only the method of detection of the magnetization direction of the permanent magnet is described using FIGS. 19 to 21, and descriptions of other components and the like are omitted.

Figure 19:
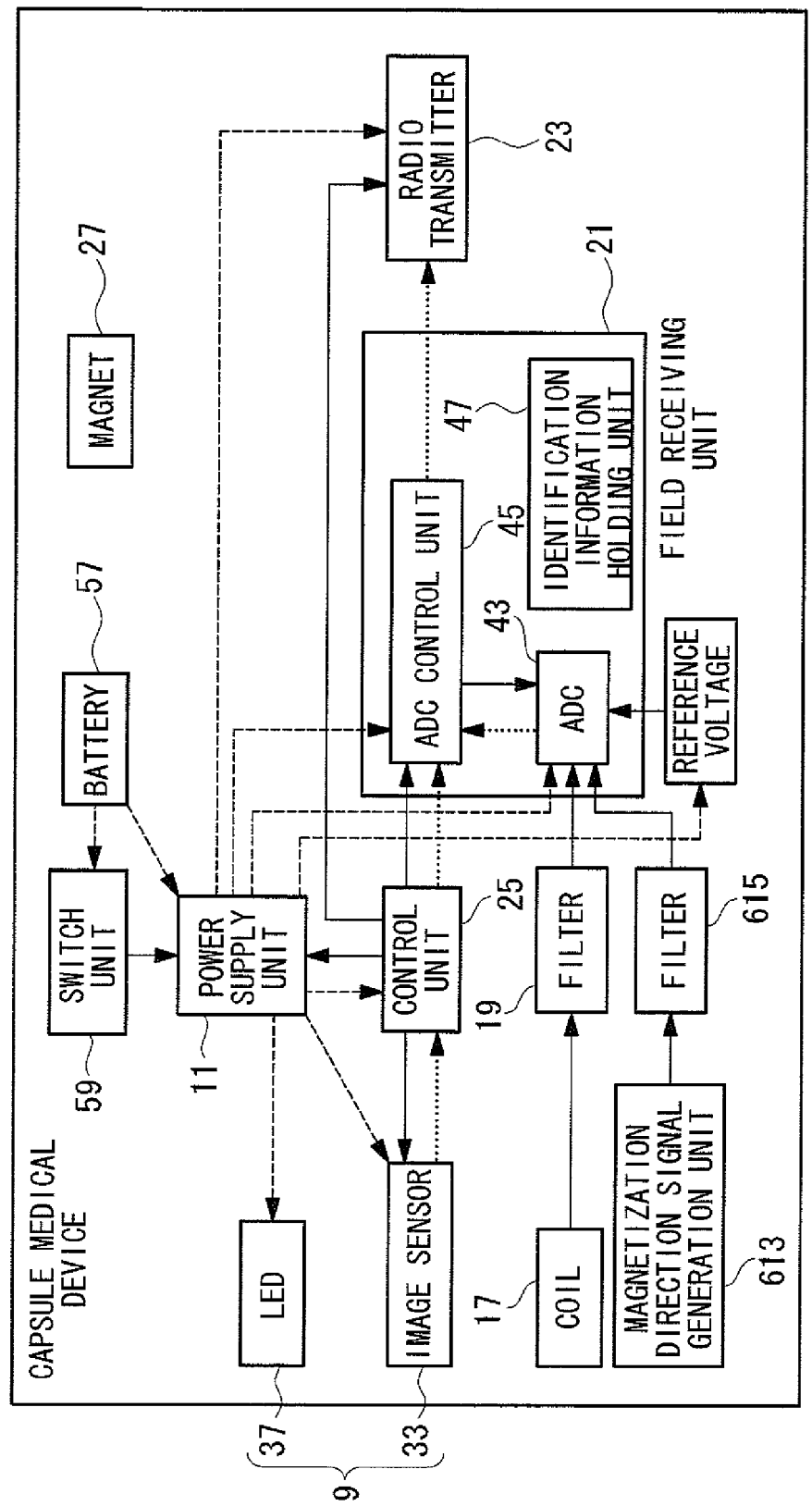
FIG. 19 shows a block diagram of a capsule medical device according to a modification of the second embodiment of the invention.

FIG. 19 shows a block diagram of a capsule medical device according to the modification.

The same components as in the second embodiment are marked with the same symbols, and descriptions of them are omitted.

As shown in FIG. 19, a capsule medical device (medical device) 603 in a capsule medical device system (medical guidance system; 601) includes a package 7, an imaging unit 9, a power supply unit 11, a magnetization direction signal generation unit 613, a signal filter 615, a coil 17, a coil filter 19, a field receiving unit 21, a radio transmitter 23, a control unit 25, and a permanent magnet 27.

The magnetization direction signal generation unit 613 generates a signal that describes the magnetization direction of the permanent magnet 27, and allows the radio transmitter 23 to transmit the signal (electromagnetic wave) that describes the magnetization direction.

The radio transmitter 23 may transmit the signal that describes the magnetization direction as described above. Alternatively, a different transmitter may be provided to transmit the signal that describes the magnetization direction without being particularly limited to this. When a different transmitter is provided, the magnetization direction of the permanent magnet 27 should preferably be parallel to the transmission direction of the signal that describes the magnetization direction. This is because the magnetization direction is easily calculated by arranging the transmitter in such a way.

The signal that describes the magnetization direction outputted from the capsule medical device system 601 may be an electromagnetic wave, a light signal, a heat signal, a sound signal, or an ultrasonic signal, which is not particularly limited.

Correspondingly, the device for outputting the signal from the capsule medical device system 601 may be the radio transmitter 23, a light emitting unit, a heating unit, a speaker unit, or an ultrasonic generator unit, which is not particularly limited.

Figure 20:
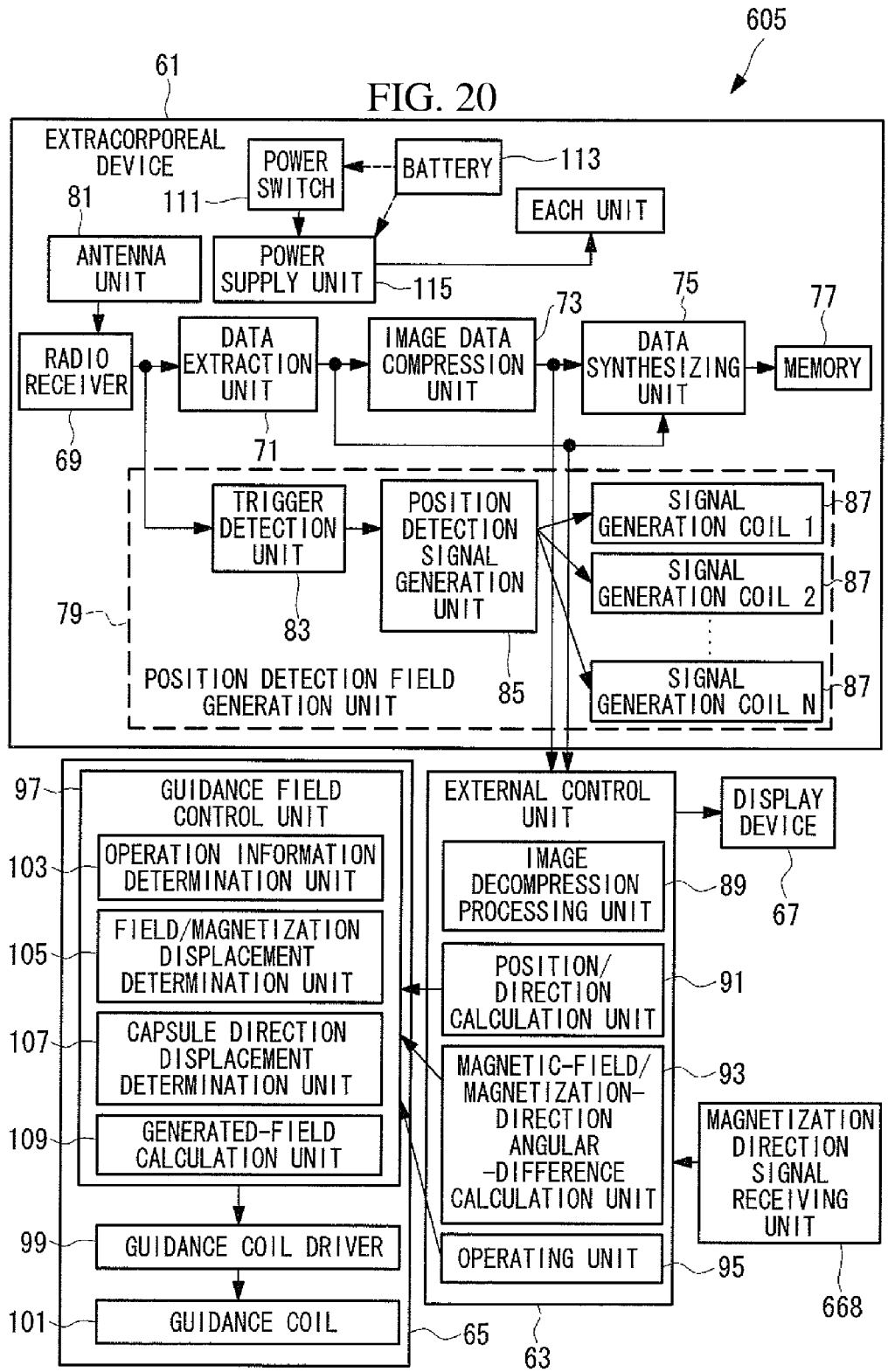
FIG. 20 shows a block diagram of an external device in the capsule medical device system according to an example of the second embodiment of the invention.

FIG. 20 shows a block diagram of an external device in the capsule medical device system according to the embodiment.

As shown in FIG. 20, the external device 605 includes an extracorporeal device 61 that generates a magnetic field M2 for position detection, an external control unit 63 that calculates the position and the direction of the capsule medical device 603, a guidance field generation unit 65 that generates a magnetic field M1 for guidance, a display device 67 that displays an image based on an image signal outputted from the external control unit 63, and a magnetization direction signal receiving unit 668 that receives a signal that describes the magnetization direction of the permanent magnet 27 in the capsule medical device 603.

The magnetization direction signal receiving unit 668 receives the signal, which is transmitted from the radio transmitter 23, that describes the magnetization direction 23.

As described before, the magnetization direction signal receiving unit 668 may be a receiver that receives an electromagnetic wave or a receiver that receives another signal such as a light, heat, sound, or ultrasonic wave signal, depending on the type of signal transmitted from the capsule medical device 603, which is not particularly limited.

For the external device 605 configured in this way, description is made on a calculation method of an angle formed between the magnetization direction of the permanent magnet 27 and the field direction of the guidance field M1 at the position of the capsule medical device 603.

FIG. 21 shows a flowchart for illustrating the calculation method of the angle formed between the magnetization direction and the field direction in the embodiment.

First, the capsule medical device 603 is powered on, and then the capsule medical device 603 is put into a body cavity from the mouth or the anus of a subject (step S201).

Then, the external device 605 acquires the position and the direction (initial position information) of the capsule medical device 603 (step S202). Since the detection method of the position of the capsule medical device 603 and the like is the same as in the first embodiment, the description of the method is omitted.

Then, the magnetization direction signal generation unit 613 of the capsule medical device 603 generates a signal that describes the magnetization direction of the permanent magnet 27. The generated signal is outputted to the signal filter 615 so that noise and the like are removed. The signal passing through the signal filter 615 is inputted to the radio transmitter 23 via the magnetization direction signal receiving unit 668. The radio transmitter 23 transmits an electromagnetic wave according to the inputted signal.

The electromagnetic wave transmitted from the radio transmitter 23 is received by the magnetization direction signal receiving unit 668 of the external device 605 (step S203).

Information about the travel direction and travel speed of the capsule medical device 603 are inputted from the operating unit 95 (step S204).

The generated-field calculation unit 109 calculates the magnetic field Bext of a guidance field M1 generated by the guidance coils 101 based on information, such as the position of the capsule medical device 603, information of the magnetization direction of the permanent magnet 27, and the travel direction of the capsule medical device 603 (step S205).

The generated-field calculation unit 109 allows the guidance coils 101 to generate a guidance field M1 based on the calculated magnetic field Bext (step S206).

Then, processing is returned to step S201, and the position and the direction of the capsule medical device 603 are acquired therein, and then the above control is repeated.

The technical scope of the invention is not limited to the above embodiments and may be variously modified or altered within a scope without departing from the gist of the invention.

For example, while the invention was described as being applicable to the capsule medical device in the embodiments, the invention is not limitedly applied to the capsule medical device performing radio communication, and for example, may be applied to a medical device system in which a permanent magnet is provided on the tip of an endoscope or a catheter so that the endoscope or the like may be propelled or guided within a body cavity.

The invention claimed is:

1. A medical guidance system comprising:
at least one guidance magnetic field generation coil provided outside of a body cavity of a subject, the at least one guidance magnetic field generation coil being configured to generate a guidance magnetic field;
at least one detection magnetic field generation coil provided outside of the body cavity of the subject, the at least one detection magnetic field generation coil being configured to generate a detection magnetic field;
a medical device configured to be provided into the body cavity of the subject, the medical device comprising:
a magnet configured to generate drive force in response to the guidance magnetic field generated by the at least one guidance magnetic field generation coil;
a magnetic sensor configured to detect a component of the detection magnetic field generated by the at least one detection magnetic field generation coil, wherein the component of the detection magnetic field is along a magnetization direction of the magnet;
an induced current generation coil configured to generate an induced current in response to the detection magnetic field generated by the at least one detection magnetic field generation coil; and
a transmitter configured to transmit both of a detection signal based on the component of the detection magnetic field detected by the magnetic sensor and an induced signal based on the induced current generated by the induced current generation coil; and
at least one processor comprising hardware, the at least one processor being configured to:
calculate a current direction of the medical device on a basis of the induced signal transmitted by the transmitter of the medical device;
determine a first displacement angle formed between an objective direction of the medical device and the current direction of the medical device;
determine a second displacement angle formed between the magnetization direction of the magnet and a direction of the guidance magnetic field at a current position of the medical device on a basis of the detection signal and the induced signal transmitted by the transmitter of the medical device; and
control a direction of the guidance magnetic field and an intensity of the guidance magnetic field generated by the at least one guidance magnetic field generation coil on the basis of the first displacement angle and the second displacement angle.

2. The medical guidance system according to claim 1, wherein the at least one processor is further configured to calculate the current position of the medical device on a basis of the induced signal transmitted by the transmitter of the medical device, and
wherein the at least one processor is configured to control the direction of the guidance magnetic field on a basis of the current position of the medical device, the current direction of the medical device, or both.

3. The medical guidance system according to claim 1, wherein the at least one processor is configured to determine the second displacement angle on a basis of a field intensity of the component of the detection magnetic field detected by the magnetic sensor and on a field intensity of the guidance magnetic field formed at the current position of the medical device.

4. The medical guidance system according to claim 1, wherein an opening direction of the induced current generation coil is perpendicular to the magnetization direction of the magnet.

5. A medical guidance system comprising:
at least one guidance magnetic field generation coil provided outside of a body cavity of a subject, the at least one guidance magnetic field generation coil being configured to generate a guidance magnetic field;
at least one position/direction detection magnetic field generation coil provided outside of the body cavity of the subject, the at least one position/direction detection magnetic field generation coil being configured to generate a position/direction detection magnetic field;

a medical device configured to be provided into the body cavity of the subject, the medical device comprising:
- a magnet configured to generate drive force in response to the guidance magnetic field generated by the at least one guidance magnetic field generation coil;
- a magnetization direction detection sensor configured to detect a magnetization direction of the magnet;
- a position/direction detection magnetic field sensor configured to detect the position/direction detection magnetic field generated by the at least one position/direction detection magnetic field generation coil; and
- a transmitter configured to transmit signals based on the magnetization direction of the magnet detected by the magnetization direction detection sensor and the position/direction detection magnetic field detected by the position/direction detection magnetic field sensor; and at least one processor comprising hardware, the at least one processor being configured to:
- calculate a current direction of the medical device on a basis of the detection result of the position/direction detection magnetic field sensor;
- determine a first displacement angle formed between an objective direction of the medical device and the current direction of the medical device;
- determine a second displacement angle formed between the magnetization direction of the magnet and a direction of the guidance magnetic field at a position of the medical device; and
- control a direction of the guidance magnetic field and an intensity of the guidance magnetic field on a basis of the first displacement angle and the second displacement angle.

6. The medical guidance system according to claim 5, wherein the at least one processor is configured to determine the second displacement angle on a basis of the magnetization direction of the magnet detected by the magnetization direction detection sensor and a field intensity of the guidance magnetic field formed at the current position of the medical device.

7. The medical guidance system according to claim 5, further comprising:
an input device configured to receive an instruction from an operator for operating the at least one guidance magnetic field generation coil.

8. The medical guidance system according to claim 5, wherein:
the position/direction detection magnetic field detection sensor is a position/direction detection magnetic field detection coil, and
an opening direction of the position/direction detection magnetic field detection coil is perpendicular to the magnetization direction of the magnet.

9. The medical guidance system according to claim 5, wherein:
the at least one guidance magnetic field generation coil is configured to generate an alternating field superimposed with the guidance magnetic field, and
the magnetization direction detection sensor is a coil having an opening direction approximately in parallel with the magnetization direction of the magnet.

10. The medical guidance system according to claim 9, wherein the at least one guidance magnetic field generation coil is configured to generate the alternating field superimposed with the guidance magnetic field at a timing when the position/direction detection magnetic field is not generated.

11. The medical guidance system according to claim 1, wherein the medical device further comprises an image sensor configured to acquire an image of the body cavity of the subject.

12. The medical guidance system according to claim 5, wherein the medical device further comprises an image sensor configured to acquire an image of the body cavity of the subject.

13. The medical guidance system according to claim 1, wherein the at least one processor is configured to:
- determine whether the first displacement angle is equal to or less than a first predetermined value,
- determine whether the second displacement angle is equal to or less than a second predetermined value,
- control the direction of the guidance magnetic field and the intensity of the guidance magnetic field generated by the at least one guidance magnetic field generation coil on the basis of whether the first displacement angle is equal to or less than the first predetermined value, and whether the second displacement angle is equal to or less than the second predetermined value.

14. The medical guidance system according to claim 5, wherein the at least one processor is configured to:
- determine whether the first displacement angle is equal to or less than a first predetermined value,
- determine whether the second displacement angle is equal to or less than a second predetermined value,
- control the direction of the guidance magnetic field and the intensity of the guidance magnetic field generated by the at least one guidance magnetic field generation coil on the basis of whether the first displacement angle is equal to or less than the first predetermined value, and whether the second displacement angle is equal to or less than the second predetermined value.

\* \* \* \* \*